(12) United States Patent
Chen et al.

(10) Patent No.: US 7,717,856 B2
(45) Date of Patent: May 18, 2010

(54) NON-TOXIC LIQUID COLUMN SPHYGMOMANOMETER

(75) Inventors: Yunquan Chen, Delta (CA); Jian Liu, Richmond (CA)

(73) Assignee: QDevice Medical Inc., Vancouver, British Columbia (CA)

( * ) Notice: Subject to any disclaimer, the term of this patent is extended or adjusted under 35 U.S.C. 154(b) by 1271 days.

(21) Appl. No.: 11/118,427

(22) Filed: May 2, 2005

(65) Prior Publication Data

US 2006/0247541 A1    Nov. 2, 2006

(51) Int. Cl.
*A61B 5/02* (2006.01)
(52) U.S. Cl. .................................. 600/497; 600/490
(58) Field of Classification Search ................ 600/403, 600/487, 497, 561, 587
See application file for complete search history.

(56) References Cited

U.S. PATENT DOCUMENTS

| | | | |
|---|---|---|---|
| 1,569,097 A | 1/1926 | MacKenzie | |
| 1,821,902 A | 9/1931 | Baum | |
| 1,905,782 A | 4/1933 | Amdursky | |
| 2,017,435 A | 10/1935 | Ey | |
| 2,361,628 A | 10/1944 | Howard | |
| 2,437,861 A | 3/1948 | Rohr | |
| 2,625,153 A * | 1/1953 | Baum | 600/487 |
| 2,669,125 A | 2/1954 | Hesse | |
| 2,698,887 A | 1/1955 | Shaw | |
| 2,866,453 A * | 12/1958 | Jewett | 600/487 |
| 4,088,058 A | 5/1978 | Flemming et al. | |
| 4,198,031 A | 4/1980 | Ezekiel et al. | |
| 4,282,881 A | 8/1981 | Todd et al. | |
| 4,436,107 A | 3/1984 | Persson | |
| 4,493,339 A | 1/1985 | Porter, Jr. | |
| 4,524,254 A | 6/1985 | Yoshida et al. | |
| 4,717,117 A | 1/1988 | Cook | |
| 5,042,473 A | 8/1991 | Lewis | |
| 5,115,830 A | 5/1992 | Harde | |
| 5,120,915 A | 6/1992 | Doherty | |
| 5,201,320 A | 4/1993 | Barker | |
| 5,634,494 A | 6/1997 | Martens | |
| 5,893,317 A | 4/1999 | Kroger | |
| 6,168,567 B1 | 1/2001 | Pickering et al. | |
| 6,283,122 B1 | 9/2001 | Adahan | |
| 6,322,052 B1 | 11/2001 | Jeuthner et al. | |
| 6,346,681 B1 | 2/2002 | Joyce et al. | |
| 6,439,506 B1 | 8/2002 | Schlegal et al. | |
| 6,485,428 B1 | 11/2002 | Enk | |
| 6,699,195 B2 | 3/2004 | Nakazawa et al. | |
| 6,752,764 B2 | 6/2004 | Oh | |

\* cited by examiner

*Primary Examiner*—Charles A Marmor, II
*Assistant Examiner*—Christian Y Jang
(74) *Attorney, Agent, or Firm*—Clark Wilson LLP

(57) ABSTRACT

A sphygmomanometer having an elongated tube, an air chamber coupled to a first end of the tube, and a liquid chamber coupled to a second end of the tube. The liquid chamber is partially filled with fluid and is couplable to a source of external pressure. An offset region located proximate the second end of the tube has a significantly reduced cross-sectional area so as to reduce the effect of fluid level changes on pressure measurement accuracy. At least one ventilation valve is coupled to the elongated tube and the air chamber and is operative to vent the elongated tube and the air chamber to atmosphere.

16 Claims, 26 Drawing Sheets

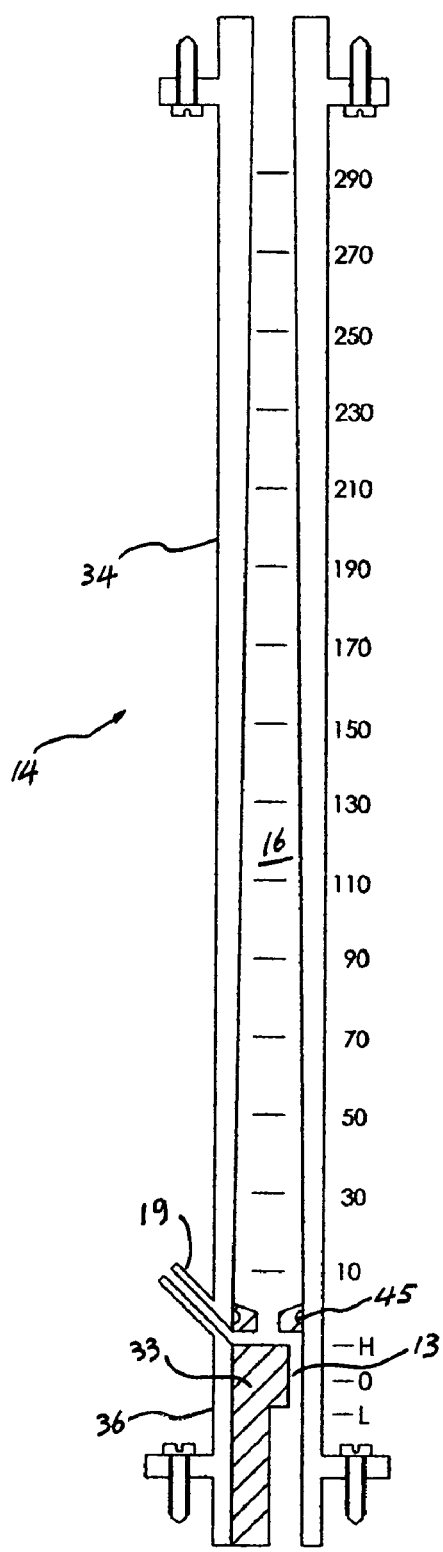
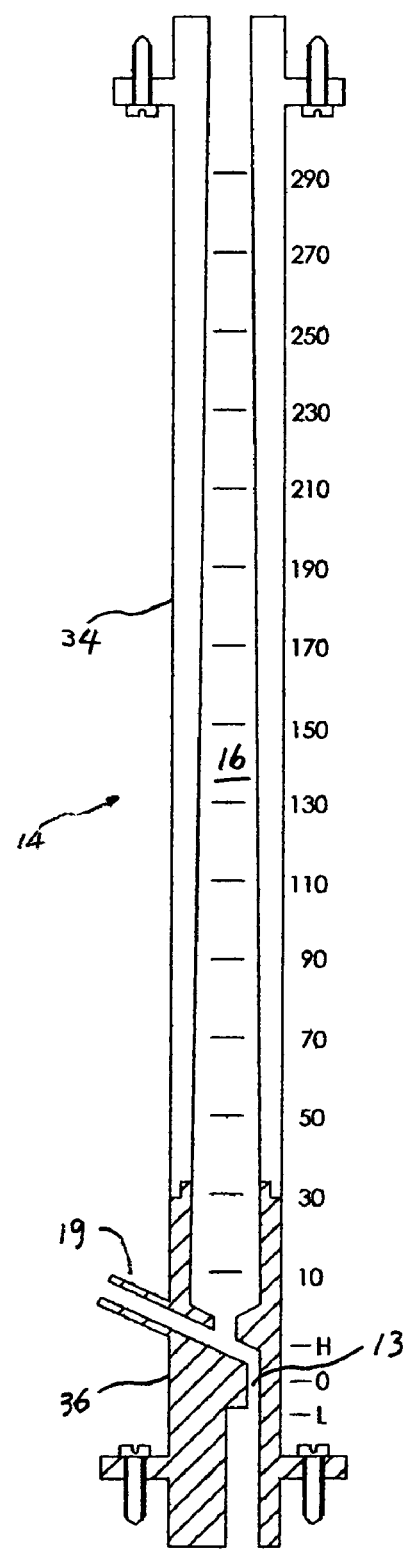
Fig. 15a
Fig. 15b

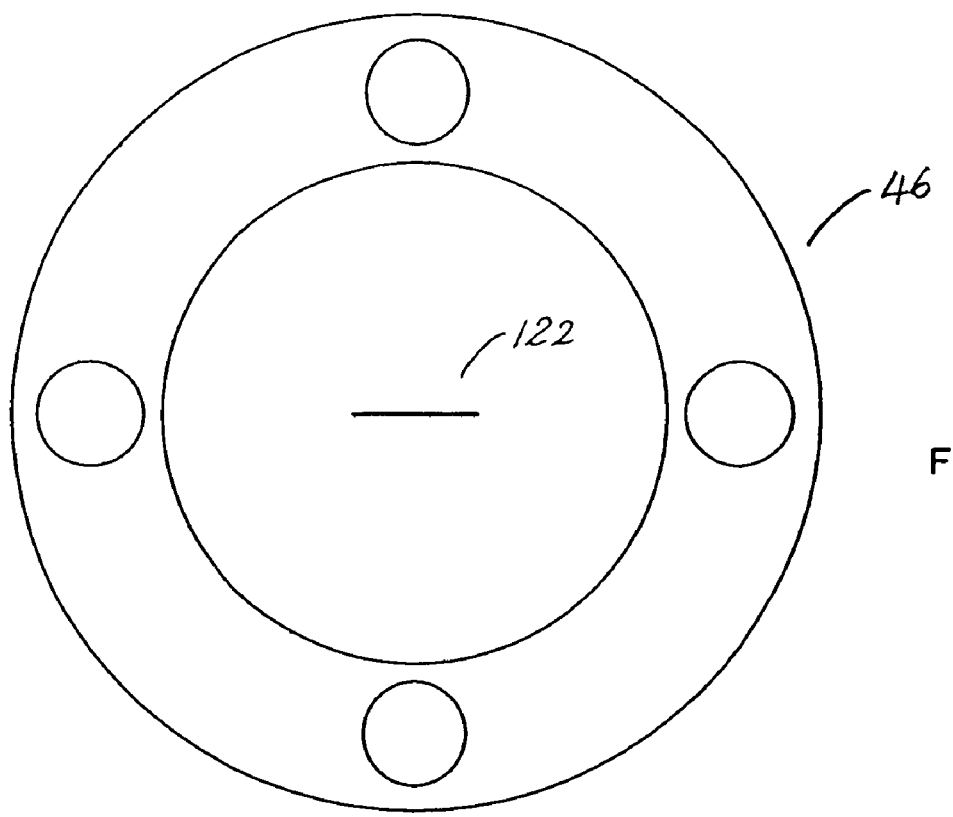
Fig. 18-a
Fig. 18-b

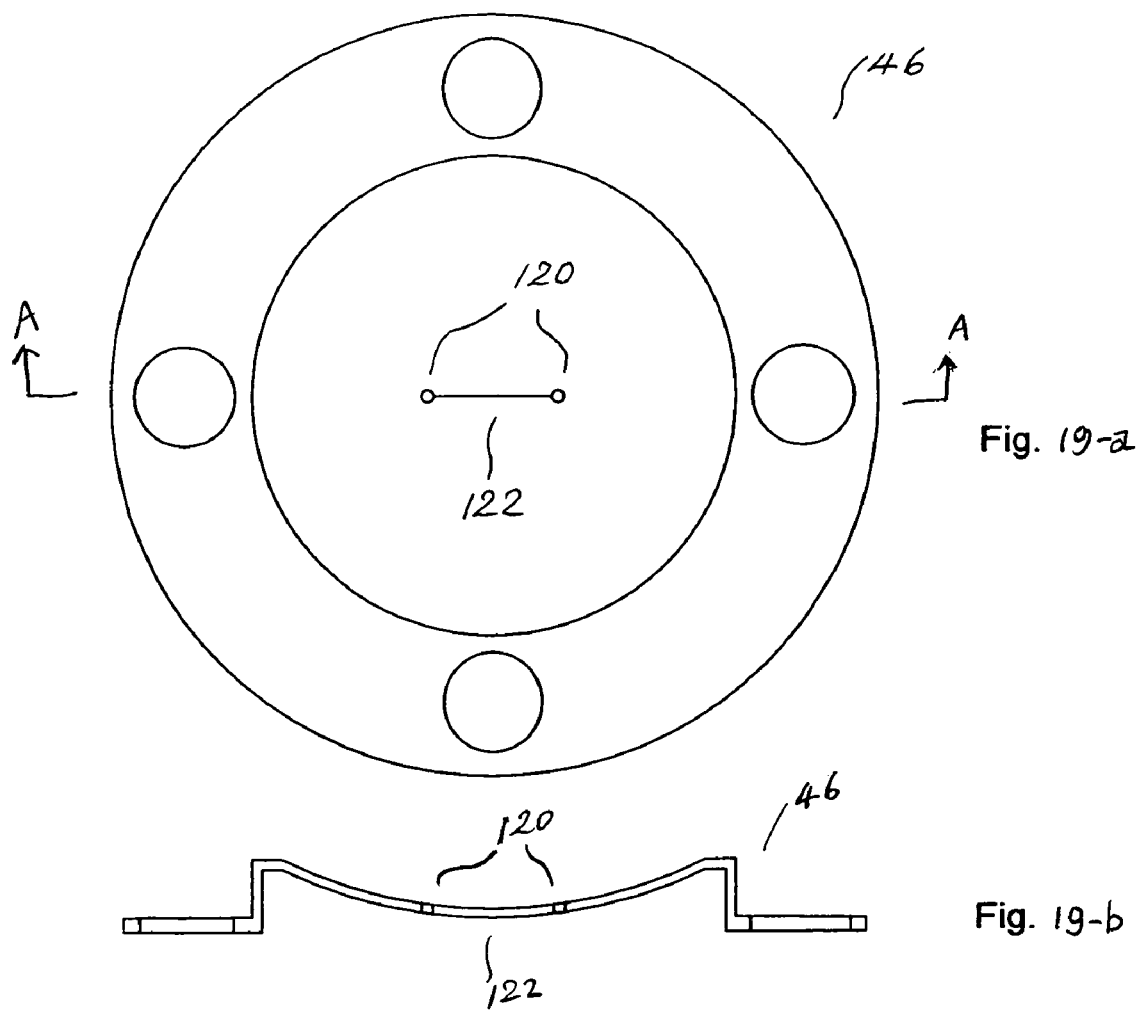
Fig. 19-a
Fig. 19-b

Changes of Standard Barometric Pressure with Altitude

| Altitude | | Standard Barometric Pressure | | |
|---|---|---|---|---|
| (Meter) | (Feet) | (mbar) | (mmHg) | (inHg) |
| 0 | 0 | 1013 | 760 | 29.92 |
| 100 | 328 | 1001 | 751 | 29.57 |
| 200 | 656 | 989 | 742 | 29.22 |
| 300 | 984 | 978 | 733 | 28.87 |
| 400 | 1312 | 966 | 725 | 28.53 |
| 500 | 1640 | 955 | 716 | 28.19 |
| 600 | 1968 | 943 | 708 | 27.85 |
| 700 | 2297 | 932 | 699 | 27.52 |
| 800 | 2625 | 921 | 691 | 27.19 |
| 900 | 2953 | 910 | 682 | 26.87 |
| 1000 | 3281 | 899 | 674 | 26.54 |
| 1100 | 3609 | 888 | 666 | 26.22 |
| 1200 | 3937 | 877 | 658 | 25.90 |
| 1300 | 4265 | 867 | 650 | 25.59 |
| 1400 | 4593 | 856 | 642 | 25.28 |
| 1500 | 4921 | 846 | 634 | 24.97 |
| 1600 | 5249 | 835 | 627 | 24.67 |
| 1700 | 5577 | 825 | 619 | 24.37 |
| 1800 | 5905 | 815 | 611 | 24.07 |
| 1900 | 6234 | 805 | 604 | 23.77 |
| 2000 | 6562 | 795 | 596 | 23.48 |
| 2100 | 6890 | 785 | 589 | 23.19 |
| 2200 | 7218 | 776 | 582 | 22.90 |
| 2300 | 7546 | 766 | 574 | 22.62 |
| 2400 | 7874 | 756 | 567 | 22.34 |
| 2500 | 8202 | 747 | 560 | 22.06 |
| 2600 | 8530 | 738 | 553 | 21.78 |
| 2700 | 8858 | 728 | 546 | 21.51 |
| 2800 | 9186 | 719 | 539 | 21.24 |
| 2900 | 9514 | 710 | 533 | 20.97 |
| 3000 | 9842 | 701 | 526 | 20.71 |
| 3048 | 10000 | 697 | 523 | 20.58 |

Fig. 27

NON-TOXIC LIQUID COLUMN SPHYGMOMANOMETER

FIELD

The present invention is related to a manometer for measuring the difference between the pressure of a gas and the ambient atmospheric pressure. In particular, the present invention is related to a sphygmomanometer, which utilizes a non-toxic liquid for measuring the pressure of air inside a cuff placed around a limb of a subject for indirect determination of the blood pressure of the subject.

BACKGROUND

Mercury column sphygmomanometers have been used for about a century and considered as the gold standard for blood pressure measurement. The measurement principle is based on the gravity of mercury, and, therefore, is accurate, reliable, easy to use and economical. The only major problem is that mercury is one of the top three toxic elements on earth. The health and environmental risks associated with mercury are very high. Many countries in the world now ban or restrict the use of mercury in healthcare and consumer products.

People have been attempting to replace mercury column sphygmomanometers with non-toxic ones. One example is an aneroid sphygmomanometer that is based on the elastic deformation property of a metal. Aneroid sphygmomanometers have not gained wide acceptance for diagnosis of hypertension or high blood pressure due to the fact that they need regular calibration. Another example is an electronic automated sphygmomanometer that is based on an empirical method called an oscillometric technique. Automated sphygmomanometers have found acceptance for home use and hospital monitoring stations. However, they have not been widely accepted for medical diagnostic purposes in clinical offices due to their inaccuracy for certain patients and certain blood pressure ranges. Medical sphygmomanometers for the diagnosis of hypertension require high accuracy and reliability. The commonly accepted accuracy is 3 mm Hg in the range of 0-200 mm Hg and 2% of the reading in the range of 200-300 mm Hg.

SUMMARY OF INVENTION

According to the invention there is provided a sphygmomanometer having an elongated tube, an air chamber coupled to a first end of the elongated tube, and a liquid chamber coupled to a second end of the elongated tube. The liquid chamber is partially filled with a liquid and coupled to a source of external pressure to be measured. A liquid offset section located proximate the second end of the elongated tube has a liquid offset channel of significantly reduced cross-sectional area so as to reduce the effect of liquid level changes on pressure measurement accuracy. At least one ventilation valve is coupled to one of the elongated tube and the air chamber and is operative to vent the elongated tube and the air chamber to atmosphere.

Preferably there is included an insert in the air chamber and one of a barometric pressure scale and an altitude scale thereon to allow adjustment of a volume of air in the air chamber according to the scale. The altitude scale is substantially linear.

The elongated tube has a pressure reading section above said liquid offset section, the pressure reading section having a substantially linear pressure scale.

Advantageously, the liquid is substantially non-toxic and is preferably water.

A pressure switch may be coupled to an external pressure source and a barometric pressure and pressure error monitor coupled to the pressure switch so that the pressure switch on closing, closes an electrical circuit coupled to the barometric pressure and pressure error monitor causing it to become activated.

A vapour loss reduction air valve is located intermediate the liquid chamber and an external pressure source. It is operative to reduce or block vapour loss when the sphygmomanometer is not in use and to permit the passage of air between said external pressure source and said liquid chamber when the sphygmomanometer is in use.

The air valve may include a diaphragm with a cut in the center to allow air to pass through when there is a pressure difference between the two sides of the diaphragm. When there is no pressure difference, the cut of the diaphragm stays almost completely closed to significantly reduce vapour loss from the liquid chamber.

The ventilation valve may be a manually operated valve in fluid communication with the air chamber. The manually operated valve has a sealing element biased against a sealing surface to keep the manual valve normally closed. In response to a manual force, the manually operated valve opens and vents the air chamber and the elongated tube to the atmosphere. In response to a rising liquid level in the elongated tube during a measurement, the manually operated valve closes tighter against the sealing surface.

The ventilation valve may be an automatically operable ventilation valve in fluid communication with the elongated tube and has a pressure input port. The automatic ventilation valve is normally open to vent the elongated tube and the air chamber and to close in response to an increase in pressure at the pressure input port.

The automatic ventilation valve may include a diaphragm responsive to pressure at the pressure input port, and a sealing disc with a first side for receiving a force from the diaphragm under pressure and a second side for sealing, upon moving in response to the force, a ventilation port coupled to the elongated tube for ventilation.

The automatic ventilation valve may include a solenoid valve having one port open to atmospheric pressure and another coupled to the elongated tube. In response to an increase in pressure the solenoid valve receives an electrical signal causing it to shut off fluid communication between the one port and the other port.

The insert may be cylindrical and slide through an o-ring at an end of the air chamber.

The insert may be a cylinder attached to a screw operative to screw the cylinder into the air chamber so as to adjust a volume of air confined by the air chamber and the cylinder.

The cylinder has a first o-ring proximate a distal end of said cylinder and a second o-ring spaced away from the first o-ring. A fluid channel extends from the external pressure source to a space between the o-rings so as to reduce the pressure differential across the first o-ring.

The insert may be an integrated insert formed by an insert holder and a variable number of insert parts mounted on the insert holder. The integrated insert is inserted into the air chamber so as to vary a volume of air in the air chamber.

One of the insert, the air chamber and the insert holder has one of altitude and barometric pressure scales thereon so as to vary a volume of air in the air chamber in accordance with the one scale.

Preferably, the volume of the air chamber is adjusted according to the equation $V=A*(P+B)$, where V is the total air volume of the elongated tube, the air chamber and the plenum that couples the elongated tube and the air chamber, P is the barometric pressure at the location where the manometer is installed, A is a scaling factor and B is a constant.

A cross sectional area of a fluid passageway in the pressure reading section of the elongated tube varies along its length so as to linearly display pressure. Preferably, the cross sectional area "A(h)" varies along its length "h" from the bottom to the top according to the equation $A(h)=C/(D+h)^2$, where C is a scaling factor and the D is a constant.

A pressure switch may be coupled to the liquid chamber and be operative to switch on the barometric pressure and pressure error monitor upon being pressurized.

The barometric pressure and pressure error monitor displays, upon being switched on, a difference between current barometric pressure and an installation barometric pressure as a percentage of an installation barometric pressure.

The pressure switch includes a diaphragm responsive to pressure to be measured, and a plunger disc with a first side for receiving a force from the diaphragm under pressure and a second side for electrically shorting two electrical contacts upon moving in response to the force.

BRIEF DESCRIPTION OF THE DRAWINGS

Further features and advantages will be apparent from the following detailed description, given by way of example, of a preferred embodiment taken in conjunction with the accompanying drawings, wherein:

FIG. 15a is a cross-sectional view of a elongated tube in which the bottom section of the elongated tube has a liquid offset insert with an o-ring seal inserted into the bottom of the tube to form a liquid offset channel for reduction of the effect of zero-offset on pressure measurement accuracy;

FIG. 15b is a cross-sectional view of an elongated tube, in which the bottom section is a single piece with fluid channels instead of an insert and a tube fitted together;

FIG. 18a is a top view of the diaphragm used in the vapor reduction air valve, in which a cut is in the center part of the diaphragm;

FIG. 18b is a cross-sectional view of the diaphragm of FIG. 18a shown with no pressure difference between the two sides of the diaphragm, in which the diaphragm has a curved center part for returning to the original shape of the diaphragm after external forces have withdrawn;

FIG. 19a is a top view of another variant of the diaphragm used in the vapor reduction air valve, in which the diaphragm has two holes at the two ends of the cut;

FIG. 19b is a cross-sectional view of the diaphragm of FIG. 19a taken along the line A of FIG. 19a;

FIG. 27 is a table showing the relationship between altitude and standard barometric pressure.

DETAILED DESCRIPTION

In the following description like parts in the same or in different figures are referred to by the same reference numbers.

Figure 1:
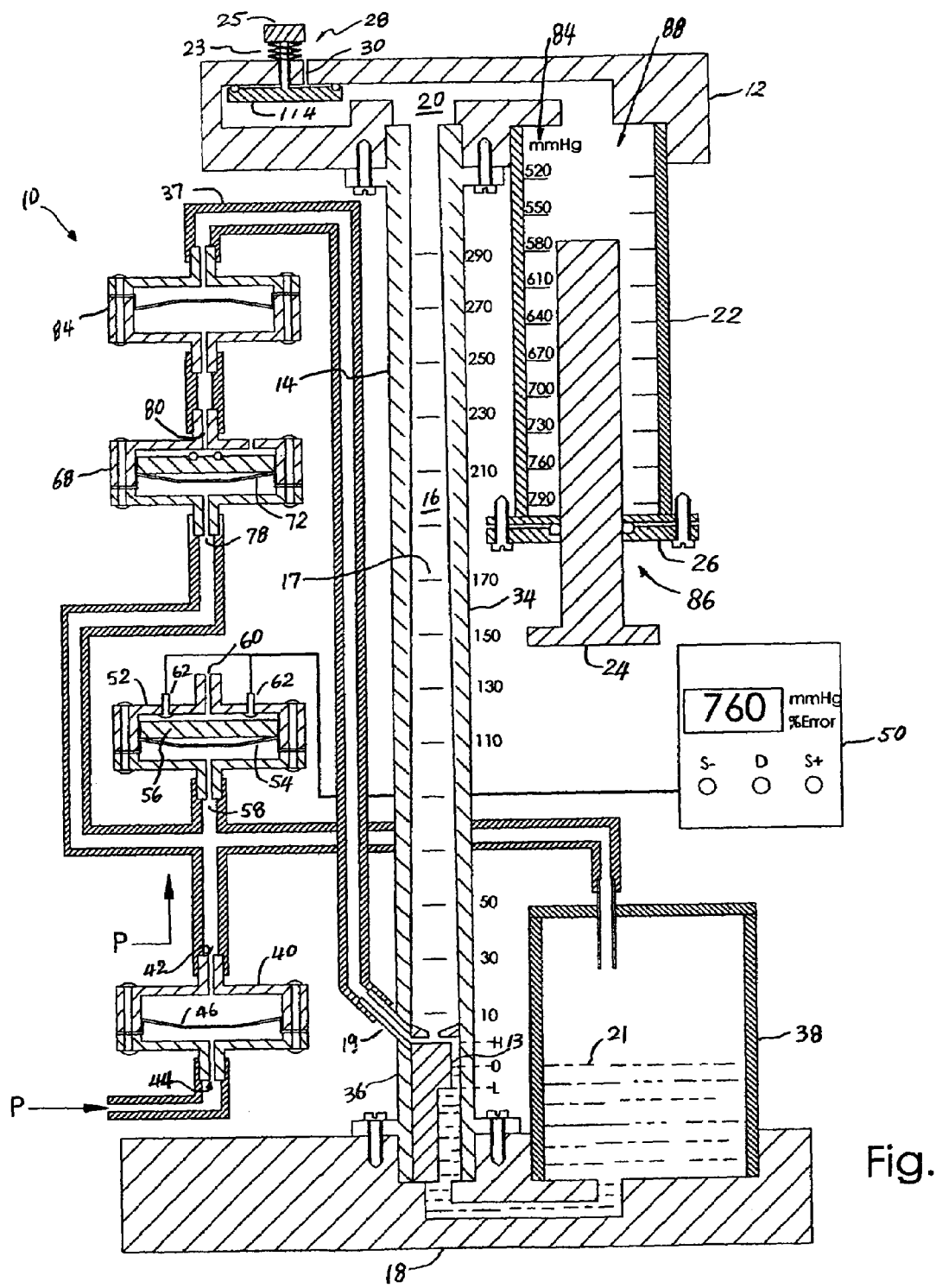
FIG. 1 is a cross-sectional view of the manometer, which includes both a manually operated and an automatic ventilation valve.

Referring to FIG. 1, a manometer 10 has top manifold 12 coupled to an upper end of an elongated tube 14. The lower end of the elongated tube 14 is coupled to a bottom manifold 18. The top manifold 12 has a plenum 20 interconnecting the fluid passageway 16 of the elongated tube 14 with an air chamber 22. An insert 24 passes through a bottom flange 26 of the air chamber 22 and is used to adjust the air volume in the air chamber 22 for installation at different altitudes. A manual ventilation valve 28 seals a bore 30 extending from atmosphere to the plenum 20. The manually operated ventilation valve 28 is normally biased closed by a bias spring 23 and opened by pressing a button 25 of the valve 28. A large disc with a large o-ring maximizes the sealing force exerted on the disc 114 by the pressure in the plenum to seal the bore 30 from the plenum 20.

The elongated tube 14 has two sections; a pressure reading section 34 and a liquid offset section 36. The pressure reading section 34 has an inside diameter that decreases with height to compensate for the non-linearity of Boyle's law. At the bottom, below the pressure reading section 34, there is a liquid offset section 36, which serves to reduce the effect of a liquid offset on pressure measurement accuracy. The liquid offset is the offset from a level of 0 mm at an applied pressure of 0 mm Hg. When the liquid offset is not zero, an error is introduced in the pressure measurement due to the volume of air taken from or given to the fluid passageway 16 by the liquid volume in the offset.

In the liquid offset section there is a liquid offset channel 13 whose cross-sectional area is reduced significantly so that when the liquid level is within the narrow liquid offset channel 13 at an applied pressure (reference to the ambient air pressure) of 0 mm Hg, a liquid level change will result in a very small air volume change inside the tube above the liquid level. Therefore, the error in pressure measurement introduced by a liquid offset within the liquid offset channel 13 will be very small.

The ratio between the cross sectional areas of the liquid offset channel 13 and the fluid passageway at the bottom of the pressure reading section 34 above the liquid offset section 36 may be between 1:5 and 1:50. Preferably, the ratio is between 1:10 and 1:30. Most preferably, the ratio is about 1:20.

Due to the use of the liquid offset channel 13, the liquid level does not need to be adjusted to the zero level in order to obtain an accurate measurement. For instance, when the cross sectional area of the narrow liquid offset channel 13 is 20 times smaller than the cross sectional area of the fluid passageway of the pressure reading section 34 above the liquid offset section 36 ("wide" channel), the liquid level offset from the zero level is 20 times less important than if the narrow channel is not used. This means that an offset of 5 mm in the narrow channel is equivalent to 0.25 mm in the normal "wide" channel. Therefore, liquid level offset in the narrow channel within a given range may be neglected. Such a given range is dependent on the ratio between the cross sectional areas of the narrow and "wide" channels, and is preferably in the range between +/−5 mm and +/−10 mm.

The liquid offset section 36 is in fluid communication with a liquid chamber 38 through the bottom manifold 18. The liquid chamber 38 contains a non-toxic liquid 21. In the present case, a non-toxic liquid is one that is not banned or restricted from use in any medical or consumer product due to its toxic nature. Water with a coloring material added is the most suitable liquid. The top of the liquid chamber 38 contains air, which communicates with the pressure to be measured.

The non-toxic liquid 21 is stored in a liquid chamber 38 and used as the pressure indicator. The non-toxic liquid 21 is also used to compress the air in the fluid passageway 16 and in the air chamber 22 when a pressure to be measured is applied on the liquid 21 in the liquid chamber 38. Preferably, the chosen liquid will not wet the inside walls of the pressure reading section 34 so that there is no residual liquid left on the walls after a measurement is completed. High surface tension of a liquid is preferable for this reason. Water is a preferred choice both for its high surface tension and for its non-toxic nature and low viscosity. Preferably, coloring material is added to water to increase its visibility. Suitable coloring materials include food-coloring additives and color inks. Suitable food-coloring additives include FD&C Green No. 3, FD&C Blue No. 1, FD&C Yellow No. 5, and FD&C Red No. 4. These food-coloring additives are stable in light. Some anti-microbial material may also be added to the water or water solution to preserve the quality of the liquid. Suitable anti-microbial materials include food preservatives that are commonly used in prepared food.

The pressure reading section 34 of the elongated tube 14 is the upper section having pressure scales 17, which are used to display the pressure to be measured using the liquid 21 as an indicator against the pressure scales 17. The elongated tube 14 is made of a translucent material. Preferred materials include translucent plastics such as acrylic and polycarbonate. Highly polished tubes made of these materials are not easily wet by water, as would be the case if glass were chosen.

A ventilation hole is located in a ventilation branch 19 of the elongated tube 14 on the liquid offset section 36 and is coupled through a ventilation tube 37 and a vapour loss reduction air valve 84 to an automatic ventilation valve 68. The vapour loss reduction air valve 84 has a diaphragm with a cut in the center part to allow air to pass through. The automatic ventilation valve 68 is normally open to allow fluid communication between the ambient air and the air in the fluid passageway 16 above the liquid offset channel 13. The pressure input port 78 of the automatic ventilation valve 68 is coupled to the liquid chamber 38 and to an external pressure source through vapour loss reduction air valve 40.

In the event either one of the vapour loss reduction air valve 84 or the automatic ventilation valve 68 fails to operate properly so that ventilation to the elongated tube is blocked, the air pressure inside the air chamber 22 and pressure reading section 34 can be brought to the ambient air pressure by pressing the button 25 of the normally closed manual ventilation valve 28. After the manual ventilation valve 28 is opened for a couple of seconds, the air pressure inside and outside the air chamber 22 will be equalized.

The air chamber 22 is used to compress air and serves as the primary pressure source to counter balance the pressure to be measured and applied onto the liquid surface inside the liquid chamber 38. The air chamber 22 is in fluid communication with the plenum 20, the pressure reading section 34 of the elongated tube 14 and the manual ventilation valve 28. The air chamber 22 has barometric pressure scales on it and an insert 24 to adjust the volume of the chamber for installation at a different altitude. Air in the pressure reading section 34 of the elongated tube 14, in the plenum 20 and in the air chamber 22 is compressed by the rising liquid levels caused by the increasing pressure applied to the liquid chamber 38 during pressure measurement. The pressure reading section 34 of the elongated tube 14 displays the pressure levels as indicated by the liquid levels. The cross sectional area of the fluid passageway 16 in the pressure reading section 34 gradually decreases from the bottom to the top so as to linearly display pressure.

Preferably, the cross sectional area A(h) of the fluid passageway 16 in the pressure reading section 34 varies along its height "h" from the bottom to the top according to the equation A(h)=C/(D+h)$^2$, where C is a scaling factor for adjusting the average thickness of the fluid passageway 16 of the pressure reading section 34 and the D is a scaling factor for adjusting the length of the pressure reading section 34 of the elongated tube 14 given a pressure measurement range. When the height h is in mm, D may be in the range between 250 and 1500. Preferably, D is in the range between 700 to 800 and the ratio between the length of the pressure reading section 34 and the pressure measurement range is roughly 290 mm:300 mmHg as is the case for mercury sphygmomanometers. In a case where a shorter or longer manometer is needed for the same pressure measurement range, the constant D may be adjusted to smaller or larger.

The air chamber volume 88 is adjusted by adjusting the length of a part of the insert 24 that is inside the air chamber 22 according to the barometric pressure scales 84 on the air chamber 22 and the barometric pressure of the place where the manometer is first installed. When an altitude of a place is known, a conversion table between the barometric pressure and altitude, which is widely available, can be used to obtain the barometric pressure at the place. FIG. 27 is an example of a conversion table.

In an alternative embodiment, the barometric pressure scales are marked on the insert (not shown here). In another alternative embodiment, altitude scales (not shown here) are marked on the air chamber 22 or the insert 24 in replacement of the barometric pressure scales.

Preferably, the volume of the air chamber is adjusted according to the equation V=A*(P+B), where V is the total air volume of the air chamber 22, the plenum 22, and the fluid passageway 16 above the liquid level of 0 mm in the elongated tube 14, P is the barometric pressure at the location where the manometer is installed, A is a volume scaling factor dependent on the air volume of the fluid passageway 16 in the pressure reading section 34 and may be determined according to Boyle's law, and B is a constant. When P is in mm Hg, B may range between 30 and 500. Preferably, B is between 150 and 300, and most preferably B is between 200 and 240.

The vapor loss reduction air valve 40 has two fluid ports 42 and 44 separated by a diaphragm 46. The diaphragm 46 has a cut in the center part. The cut is almost closed when there is no pressure difference between the two sides of the diaphragm 46. This significantly reduces evaporation of the liquid 21 in the liquid chamber 38. When a pressure difference develops between the two sides of the diaphragm 46, the positive pressure side pushes open the cut of the diaphragm 46 and air flows from the high-pressure side to the low pressure side. As soon as the pressure difference disappears, the cut of on the diaphragm 46 reaches roughly a closed position again.

The barometric pressure and measurement error monitor 50 is useful when the manometer 10 is installed in a place with an altitude different from the factory default. The manometer 10 must be installed properly in order for it to function accurately. Each 7 mm Hg difference in barometric pressure at a barometric pressure of 700 mm Hg will generate a measurement error of 1% of the reading. When first installing the manometer 10 at a location, one may use the barometric pressure reading of the barometric pressure and pressure error monitor 50 to guide the installation of the insert 24 in the air chamber 22 according to the barometric pressure scales 84 on the air chamber 22. For instance, when the barometric pressure reading on the barometric pressure and measurement error monitor 50 is 574 mm Hg et a location where the manometer 10 is to be installed, the insert 24 shall be inserted into the air chamber 22 till the top of the insert reaches the division of 574 mm Hg on the barometric pressure scales (minor divisions are not shown in FIG. 1) on the air chamber 22. Then, a set button S– or S+ on the barometric pressure and measurement error monitor 50 shall be pressed multiple times till the default installation barometric pressure has been changed to 574 mm Hg.

The barometric pressure and measurement error monitor 50 is also used to calculate the percentage error of measurement caused by barometric pressure changes after installation. After the manometer 10 has been installed in a place at an installation barometric pressure, weather change may cause the barometric pressure to change to a different pressure than the installation barometric pressure. Such a change has the same effect on measurement accuracy as the installation barometric pressure. That is, every 1% change in barometric pressure caused by weather changes after installation will result in 1% error in the measurement. This measurement error may be corrected by the use of the barometric pressure and measurement error monitor 50. The barometric pressure and measurement error monitor 50 is automatically turned on every time the manometer 10 is used. This is achieved by the use of the pressure switch 52.

The barometric pressure and measurement error monitor 50 is used to show barometric pressure or measurement error as a percentage of the reading. In FIG. 1, the barometric pressure is shown whereas in FIG. 2 the measurement error as a percentage of the reading is shown. The manometer 10 comprises a barometer with memory and computing means for providing weather change information and pressure measurement errors caused by weather changes. The barometer remembers the barometric pressure at the time the manometer 10 is installed. When weather changes cause a change in barometric pressure, the manometer 10 generates a pressure reading error due to the barometric pressure change. This error is proportional to the barometric pressure change. The barometer will first record the current barometric pressure. Then, it will compare the current barometric pressure with the installation barometric pressure stored in the barometer. The difference will be divided by the installation barometric pressure and will be provided as a percentage. This percentage in barometric pressure change is the same as the percentage error of the sphygmomanometer pressure measurement. The user may use this number to correct the manometer reading and obtain an accurate measurement of the applied pressure.

Note that the polarity of the barometric pressure change is the opposite of the polarity of the sphygmomanometer reading error. For instance, if the barometric pressure change is minus 1%, the sphygmomanometer readings would be over the true value by 1%, and need to be reduced by 1% to obtain the true value. In other words, when the barometric pressure and measurement error monitor shows 1%, the reading of the sphygmomanometer needs to be reduced by 1% of the reading; Similarly, when the barometric pressure and measurement error monitor shows +1% or 1%, the reading of the sphygmomanometer needs to be increased by 1% of the reading.

The pressure switch 52 is a normally open switch. It has a diaphragm 54 inside the switch. An electrically conductive disc plunger 56 sits on the diaphragm. The pressure switch has one pressure input port 58 and a ventilation port 60. When a pressure is applied to the pressure input port 60, the pressure pushes the diaphragm 54 up and brings the electrically conductive disc plunger 56 into contact with two conductors 62 mounted on the pressure switch 52 and closes the switch.

The applied pressure to be measured either directly through the pressurized air or indirectly through the pressurized liquid 21 (not shown) in the liquid chamber 38 may activate the pressure switch 52. When the pressure switch 52 is activated, it switches on and triggers the barometric pressure and measurement error monitor 50 to turn on automatically from an idle state. This automatic feature is useful for physicians who want to save every second in a busy schedule. It also ensures that measurement error information is always presented to the user to prevent a potentially large measurement error from going unnoticed.

The advantage of the above pressure switch 52 is its simplicity and low manufacturing cost. An alternative commercially available pressure switch can also be used although it may be much more expensive. One example of such a commercially available pressure switch is a pressure switch in the PSF102 series made by World Magnetics in Traverse City, Mich., USA.

In operation, a cuff (not shown) is normally wrapped around an upper arm of a subject. The cuff communicates with the liquid chamber and the pressure in the cuff is displayed on the pressure reading section 34 of the elongated tube 14. The cuff is in fluid communication with a manual or automated air pump (not shown), a manual or automatic deflation valve (not shown) and the liquid chamber 38 through the vapour loss reduction air valve 40.

Initially, the air pressure in the fluid passageway 16, the plenum 20, and the air chamber 22 is at atmospheric pressure due to the automatic ventilation valve 68 being open. In an inflation phase, the air pump (not shown) is operated and the pressure in the cuff increases. The cut in the diaphragm 46 opens and transmits airflow from the port 44 to the port 42. The pressure above the liquid 21 in the liquid chamber 38 increases and causes the liquid level in the elongated tube 14 to rise. The pressure also causes the automatic ventilation valve 68 to close the ventilation port 80 and the pressure switch 52 to turn on the barometric pressure and measurement error monitor 50 from an idle state. As the liquid 21 rises along the fluid passageway 16 in the reading section 34 it compresses the air in the fluid passageway 16, the plenum 20 and the air chamber 22 so that a pressure is developed inside the fluid passageway 16, the plenum 20 and the air chamber 22. This air pressure plus the weight of the liquid counterbalances the pressure in the cuff. The liquid 21 also rises in the ventilation tube 37 and compresses the air in the ventilation tube 37 and the vapour loss reduction air valve 84 after the automatic ventilation valve 68 has closed the ventilation port 80. The pressure developed in the ventilation tube 37 prevents the liquid from reaching the vapour loss reduction air valve 84 and the automatic ventilation valve 68. After the pressure in the cuff has reached certain level, the air pump is stopped and the deflation valve (not shown) is operated to deflate the pressure in the cuff.

In the deflation phase, the cut in the diaphragm 46 opens and transmits airflow from the port 42 to the port 44. The pressure of air above the liquid plus the weight of the liquid in the elongated tube 14 causes the liquid level in the elongated tube 14 to fall. As the liquid 21 falls along the fluid passageway 16 the air in the fluid passageway 16, the plenum 20 and the air chamber 22 expands and the air pressure decreases so that at any moment the cuff pressure is always balanced by the air pressure inside the elongated tube and the weight of the liquid column. The air pressure in the ventilation tube 37 also causes the liquid 21 to fall in the ventilation tube 37 until an initial start level has been reached. When the pressure in the cuff falls back to ambient air pressure, the automatic ventilation valve 68 re-opens the ventilation port 80, and the pressure switch 52 turns open. The barometric pressure and measurement error monitor 50 turns off to an idle state in a given amount of time after the pressure switch 52 has turned open.

During the deflation phase, an operator determines the blood pressure of a subject by listening to the sounds of the artery over which the cuff is wrapped on and reading the liquid levels at which artery sounds are heard. After the blood pressure readings have been obtained in this manner, the operator further reads the percentage measurement error displayed on the barometric pressure and measurement error monitor 50 and corrects the blood pressure readings if needed.

Figure 2:
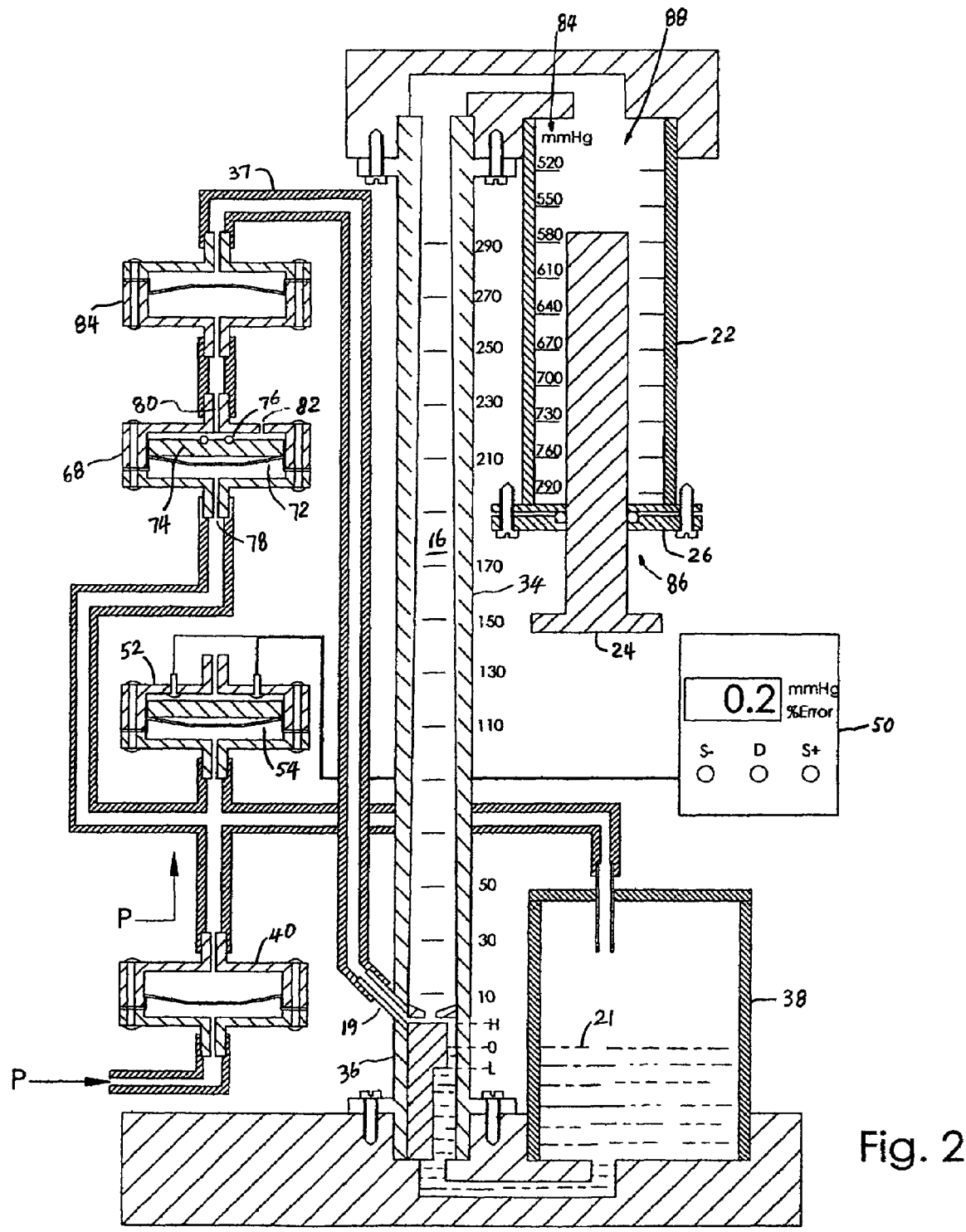
FIG. 2 is a cross-sectional view of a variant of the manometer of FIG. 1 incorporating an automatic ventilation valve.

FIG. 2 shows a manometer, as in FIG. 1, but with only an automatic ventilation valve 68 and no manual one. The automatic ventilation valve 68 is a normally open valve. It has a diaphragm 72 inside the valve. A plunger disc 74 with an o-ring seal 76 is sitting on the diaphragm 72. The automatic ventilation valve 68 has one pressure, input port 78 and one ventilation port 80 and one ventilation hole 82. The ventilation port 80 is used to communicate with the fluid passageway 16 through the vapor loss reduction air valve 84. The ventilation hole 82 of the automatic ventilation valve 68 is used to vent the fluid passageway 16, the plenum 20 and the air chamber 22 to the ambient atmosphere when the liquid level in the elongated tube 14 is below the ventilation branch 19 of the elongated tube 14.

The difference between the area of the plunger disc 74 and the area covered by the o-ring seal 76 is significant large so that the o-ring seal 76 will seal well even with a low input pressure at the pressure input port 78. The diameters of the plunger disc 74 and the top of the diaphragm 72 are preferably larger than 12 mm, and most preferably larger than 25 mm. The diameter of the o-ring seal 76 is preferably between 2 mm and 7 mm and most preferably about 4.3 mm when the diameter of the plunger disc 54 is about 25 mm.

When a pressure is applied to the pressure input port 78, the pressure pushes the diaphragm 72 up and brings the plunger disc 74 up with it so that the o-ring seal 76 on the plunger disc 74 seals the ventilation port 80. When the applied pressure drops back to the ambient air pressure, the gravity of the plunger disc 74 pulls down the plunger disc 74 and re-opens the ventilation port 80. Since the automatic ventilation valve 68 relies on gravity to re-open, the automatic ventilation valve 68 must be mounted vertically to keep it normally open. In order to mount the automatic ventilation valve 68 in other orientations than the vertical orientation as shown in FIG. 2, one or more bias springs (not shown) may be placed between the plunger disc 74 and the inside wall facing the plunger disc 74 to keep the valve normally open.

The applied pressure may be the pressure to be measured as shown in FIG. 2. The applied pressure may also be a pressure of the liquid 21 in the liquid chamber 38 (not shown). The liquid 21 in the liquid chamber 38 develops a pressure when the pressure to be measured is applied to the liquid chamber 38.

The automatic ventilation valve 68 provides air ventilation to the fluid passageway 16 through a ventilation tube 37 attached to the branch 19 close to the upper end of the liquid offset section 36 of the elongated tube 14. Ambient air can enter or exit the fluid passageway 16 above the liquid level inside the elongated tube 14, the plenum 20 and the air chamber 22 freely through the ventilation hole 82 of the automatic ventilation valve 68 when the pressure applied to the liquid 21 in the liquid chamber 38 is just ambient air pressure. The automatic ventilation valve 68 will automatically close after measurement has started.

Figure 3:
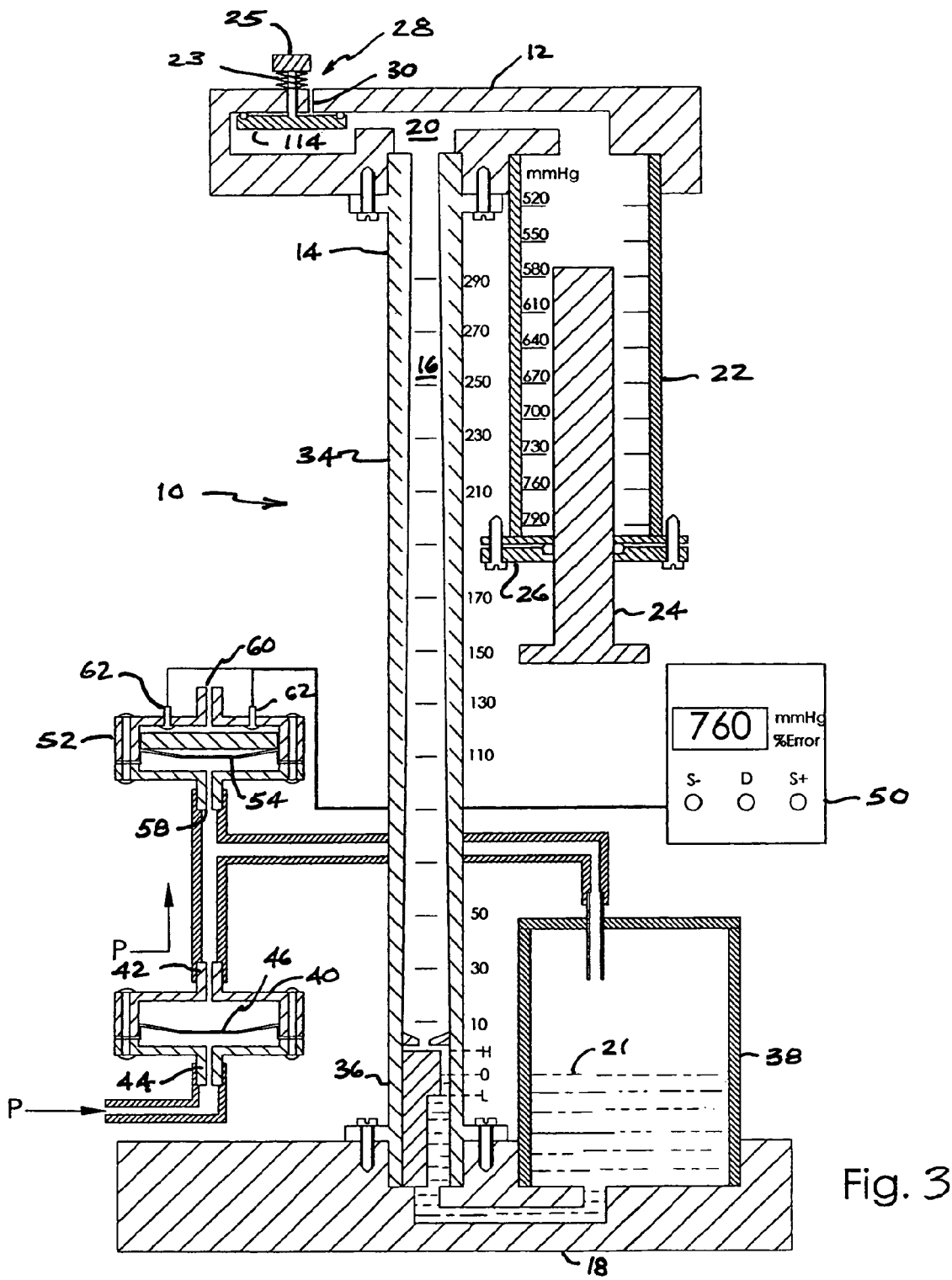
FIG. 3 is a cross-sectional view of the manometer with a manual ventilation valve.

FIG. 3 shows a manometer, as in FIG. 1, but with only a manual ventilation valve 28 and no automatic one. This embodiment has the advantage of costing less to make, but has the disadvantage that before a measurement can be started, likely the button 25 of the manually operated ventilation valve 28 needs to be pressed down for a couple of seconds to vent the elongated tube 14, the plenum 20 and the air chamber 22 to the ambient atmosphere in order for the liquid level in the elongated tube 14 to return to the liquid offset channel 13.

Figure 4:
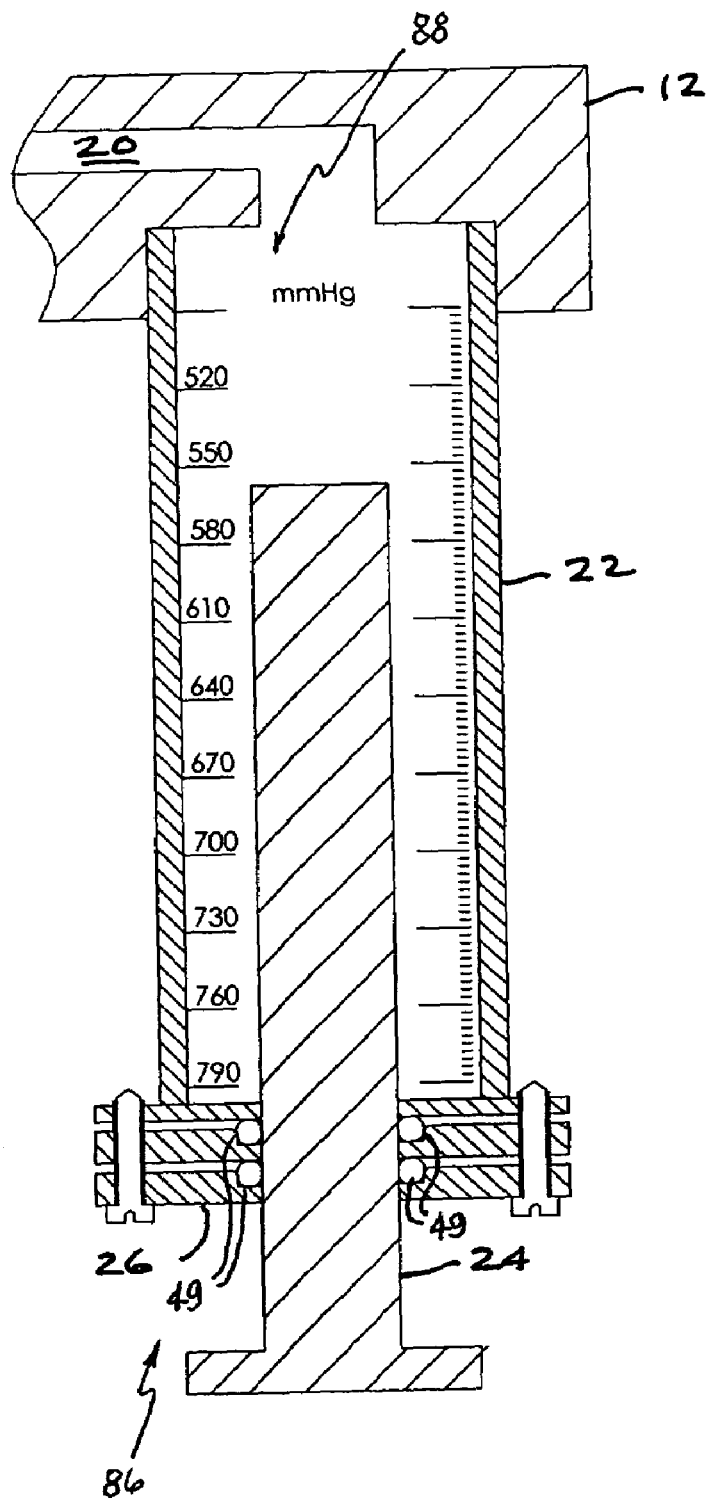
FIG. 4 is a cross-sectional view of an air chamber having two o-rings to enhance the seal around the rod insert.

Referring to FIG. 4, an air chamber 22 is shown having double O-rings 49 to enhance sealing around the insert 24. The insert 24 is used to vary the air volume of the air chamber 22. The air chamber 22 is substantially elongated having an insert end 86 and a manifold end 88 with a length of between 50 mm and 300 mm. Preferably, the length of the air chamber 22 is between 100 mm and 150 mm. In one embodiment, the air chamber 22 is made of translucent material and has one, two or three barometric pressure scales on it. Preferably, the longitudinal axis of the air chamber 22 is positioned vertically.

The barometric pressure scale is on the air chamber 22 but could also be on the insert 24. The barometric pressure scale may also be replaced with an altitude scale using a table of conversion between standard barometric pressure and altitude.

Preferably, the altitude range is divided into three altitude zones, namely, (−330)-1000 m, 1000-2000 m, and 2000-3000 m. The corresponding standard barometric pressure is roughly 790 mm Hg-680 mm Hg, 680 mm Hg-600 mm Hg, and 600 mm Hg-520 mm Hg, respectively. See FIG. 27 for a more detailed relationship between altitude and standard barometric pressure.

It is preferable that the resolution of the barometric pressure scales is in the range of 2 to 4 mm Hg, most preferably 2 mm Hg. The latter corresponds to a 0.26% reading error caused by installation resolution when the altitude is at sea level (760 mm Hg) or 0.38% when the altitude is at 3000 m (526 mm Hg).

Figure 5:
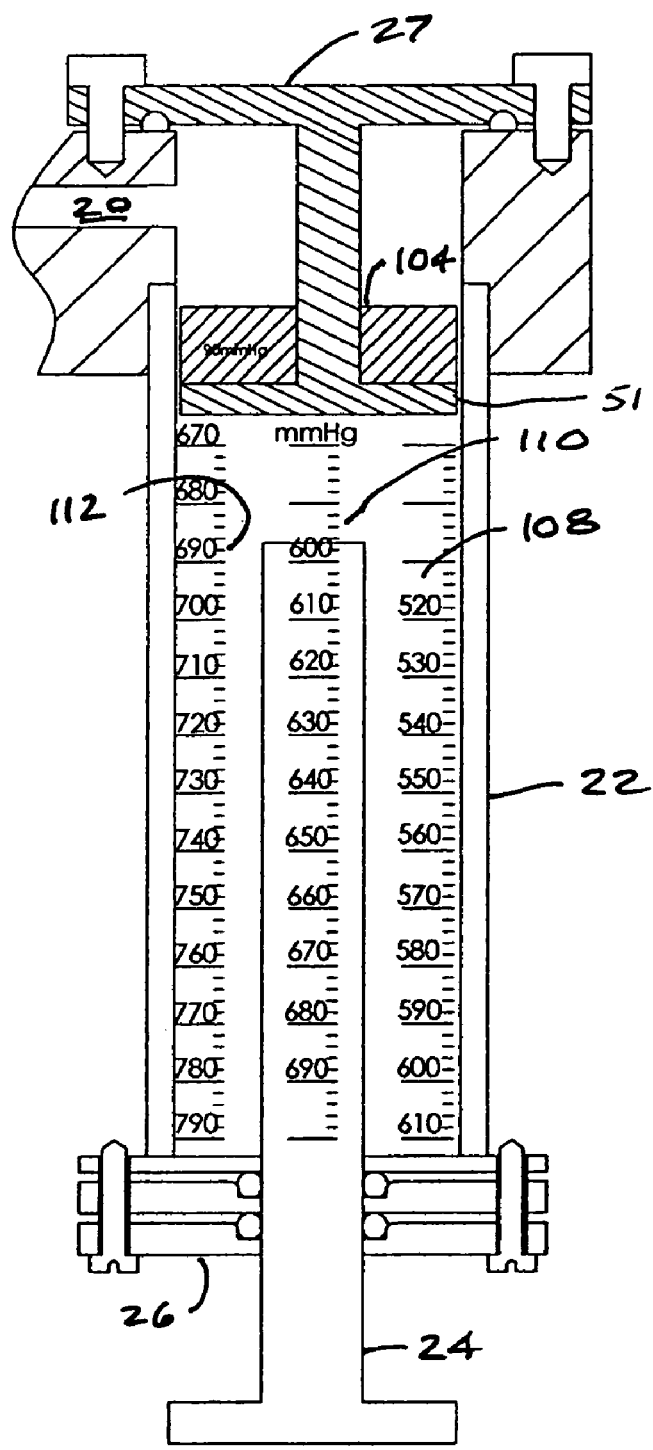
FIG. 5 is a cross-sectional view of an air chamber in which the barometric pressure range is covered in three barometric pressure scales instead of one as shown in FIG. 4.

FIG. 5 shows the use of a fixed insert 104 in combination with a variable rod insert 24 to achieve fine adjustment of the air volume in the air chamber 22. Zero to 2 pieces of a fixed insert 104, each equivalent to a rod insert for a drop of 90 mm Hg of barometric pressure, may be placed on the shelf 51. If there is no fixed insert 104, the left side barometric pressure scale is applicable. If one fixed insert 104 is used, the barometric pressure scale in the middle will be used. If two fixed inserts are used, the right scale will be used. This way, the length of the rod insert 24 is reduced to about a third without reducing the resolution of the altitude installation or equivalently, the resolution of the altitude installation is increased to about three times without increasing the length of the rod insert 24.

Figure 6:
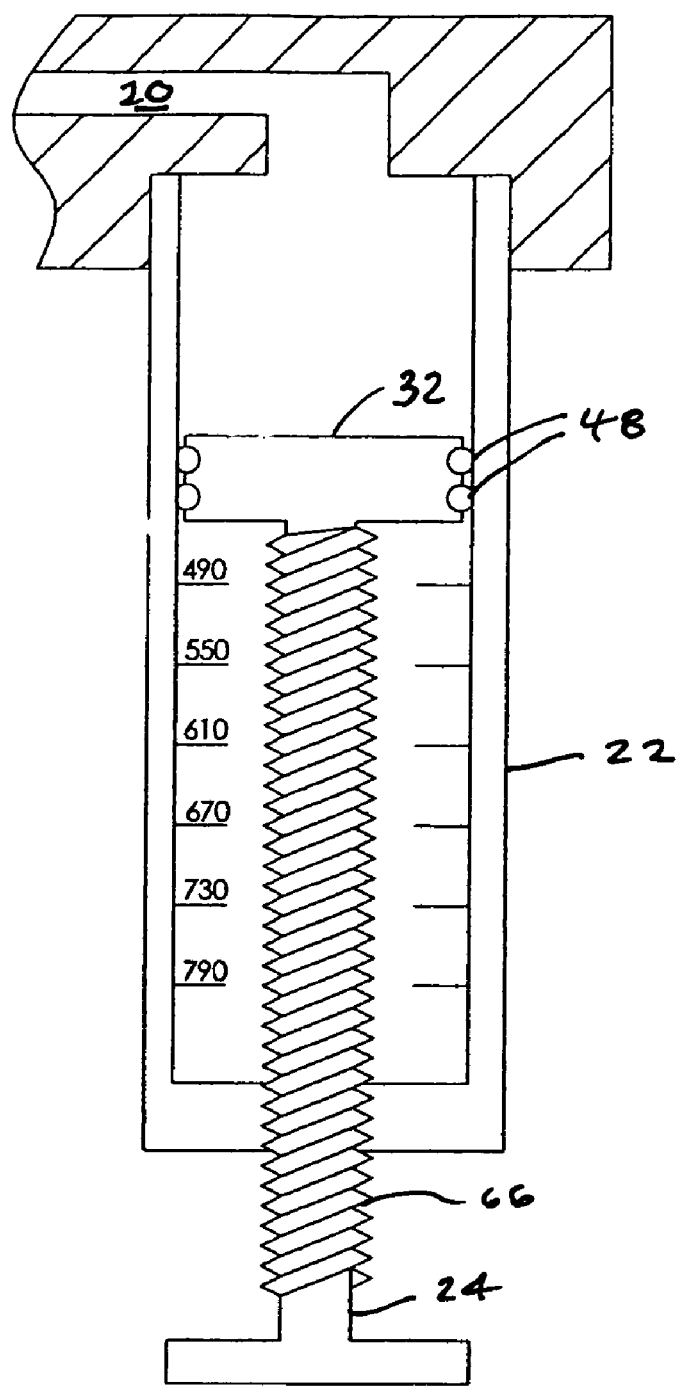
FIG. 6 is a cross-sectional view of another variant of the air chamber, in which the insert is a cylinder with a screw to position the cylinder.

FIG. 6 discloses an air chamber 22 with an variable insert 24 having a cylinder 32 that travels along the length of the air chamber 22 in sealing contact by two o-rings 48 against the cylindrical sidewall of the air chamber 22 in response to rotation of a screw 66 passing through an insert end of the air chamber 22. This arrangement provides a low resolution with only one barometric pressure scale.

Figure 7:
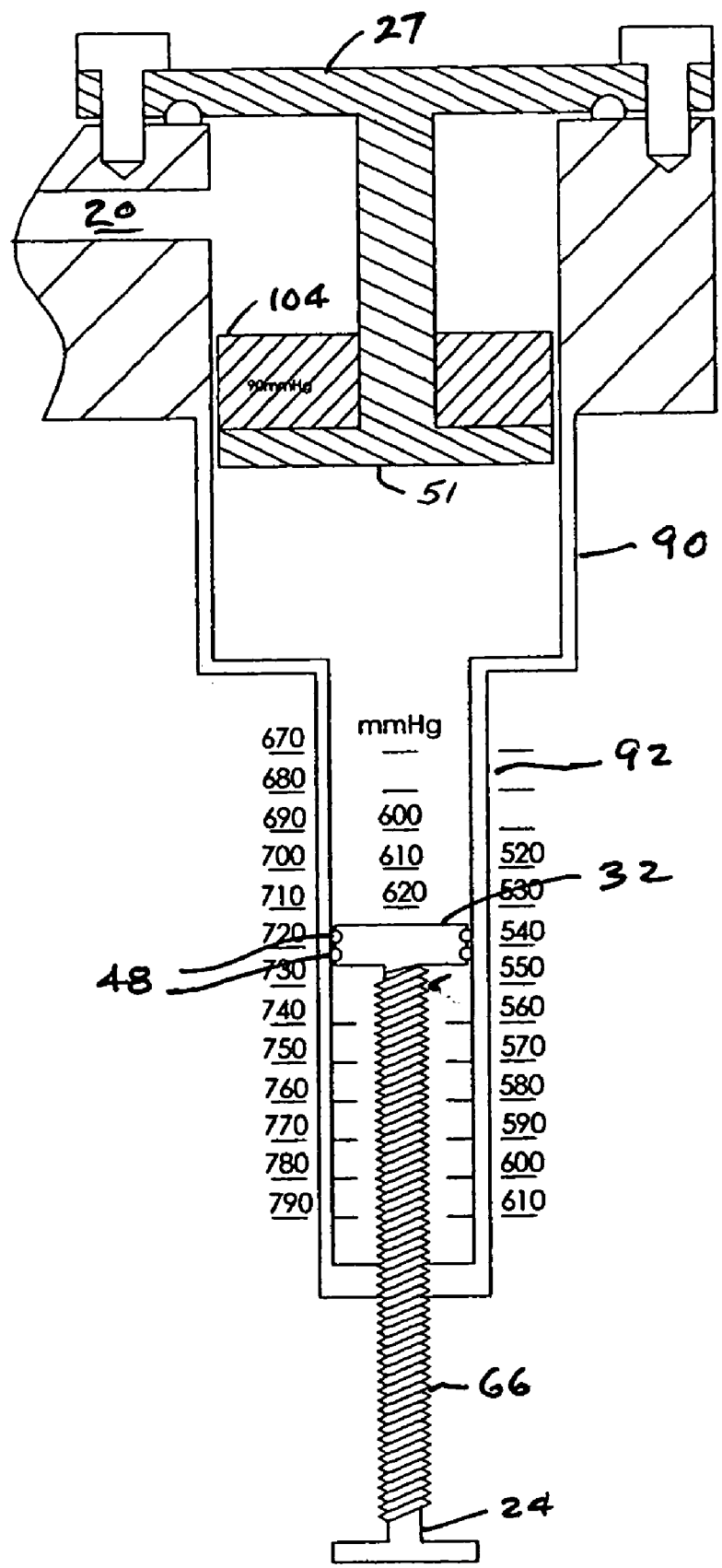
FIG. 7 is a cross-sectional view of yet another variant of the air chamber, in which the air chamber is divided into a larger and a smaller chamber to increase the resolution of barometric pressure scales.

FIG. 7 shows the use of a fixed insert 104 in combination with a variable cylinder insert 24 to achieve fine adjustment of the air volume in the air chamber 22. The air chamber 22 of FIG. 6 is separated into a main chamber 90 and a cylinder chamber 92 at the end of the main chamber 90 in FIG. 7. This embodiment provides: increased resolution over that of FIG. 6.

Figure 8:
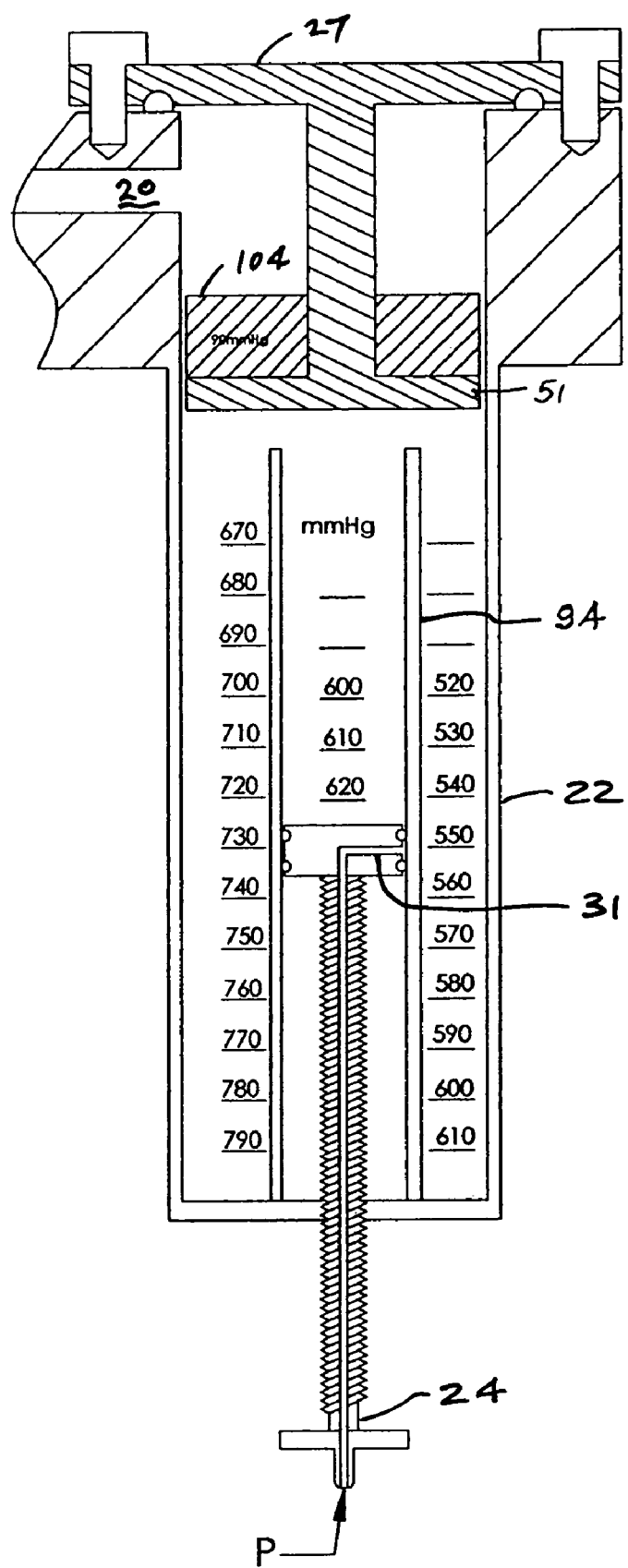
FIG. 8 is a cross-sectional view of another variant of the air chamber, in which the smaller part of the air chamber is located inside the large part of the air chamber instead of at the bottom as shown in FIG. 7.

FIG. 8 discloses an embodiment with a cylinder chamber 94 inside a main chamber 22. An air channel 31 passes through insert 24 and provides an equalization pressure to the space between a top and bottom o-ring seal to reduce differential pressure between the inside of the air chamber 22 and the air channel 31 so that leakage across the top o-ring seal is minimized. The equalization pressure may be the pressure to be measured. The difference between the pressure to be measured and the pressure inside the air chamber 22 is small. The pressure difference is caused by the weight of the liquid column inside the elongated tube 14 during a measurement. Therefore the maximum difference is about 300 mm H$_2$O or about 22 mm Hg when the liquid 21 is water.

Figure 9:
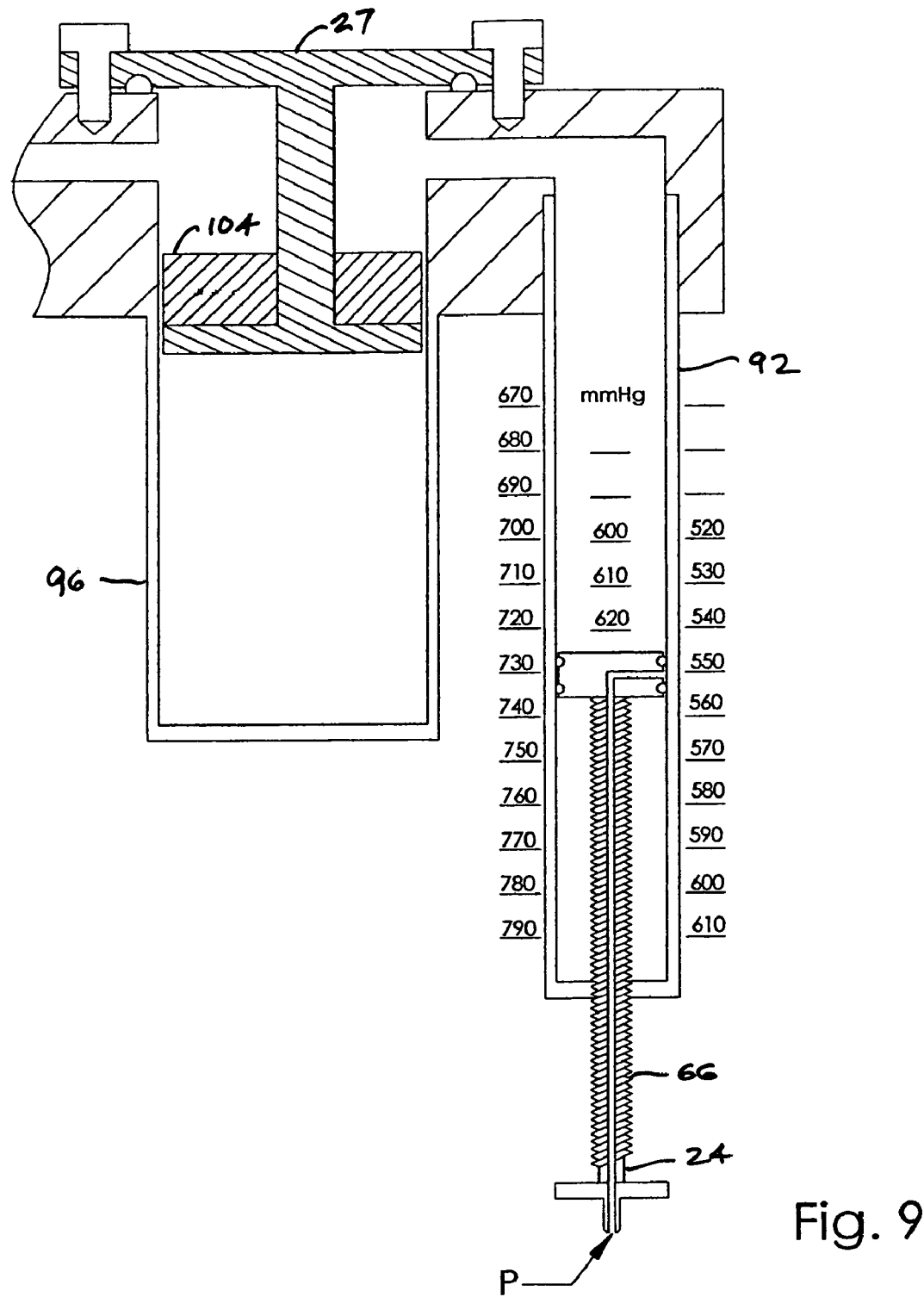
FIG. 9 is a cross-sectional view of another variant of the air chamber, in which the smaller part of the air chamber is located in parallel with the large part of the air chamber instead of inside the larger part as shown in FIG. 7.

FIG. 9 discloses an embodiment in which a cylinder chamber 92 is outside and adjacent to a major air chamber 96.

Figure 10:
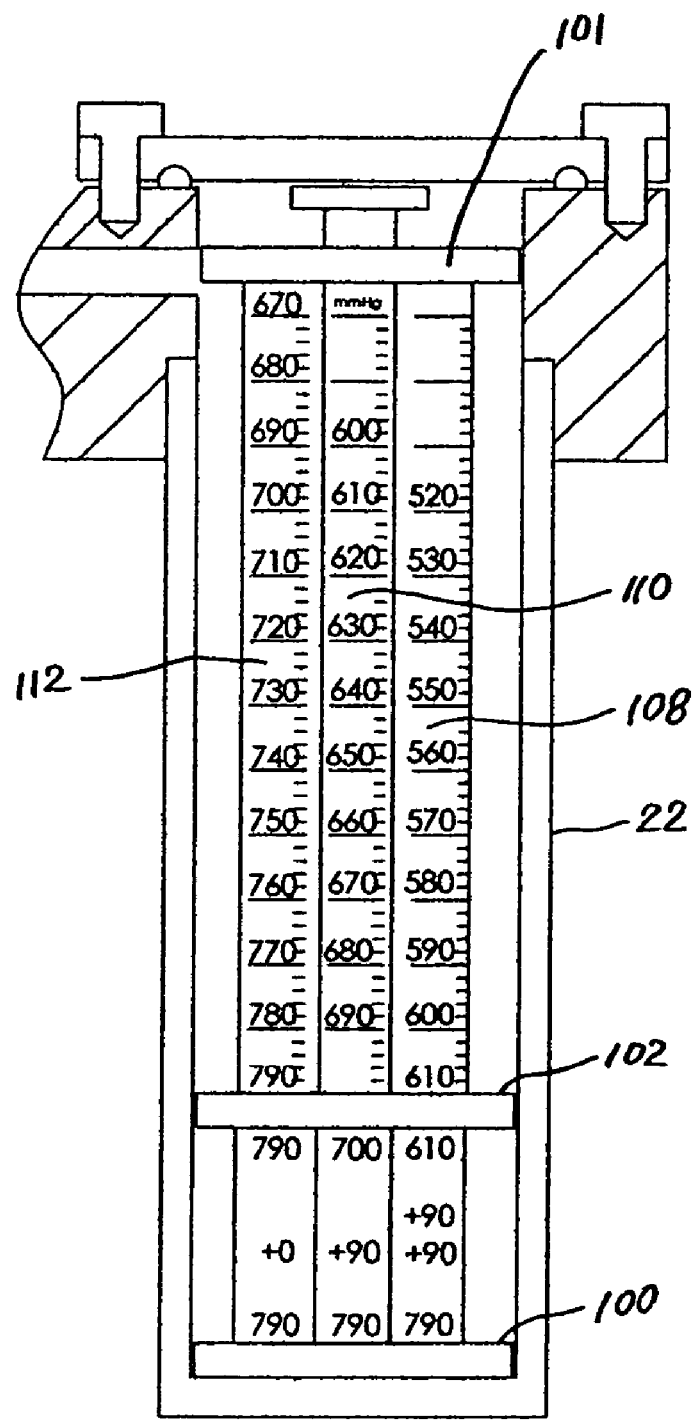
FIG. 10 is another variant of the air chamber, in which an insert holder with three barometric pressure scales on it is enclosed in the air chamber.
Figure 11:
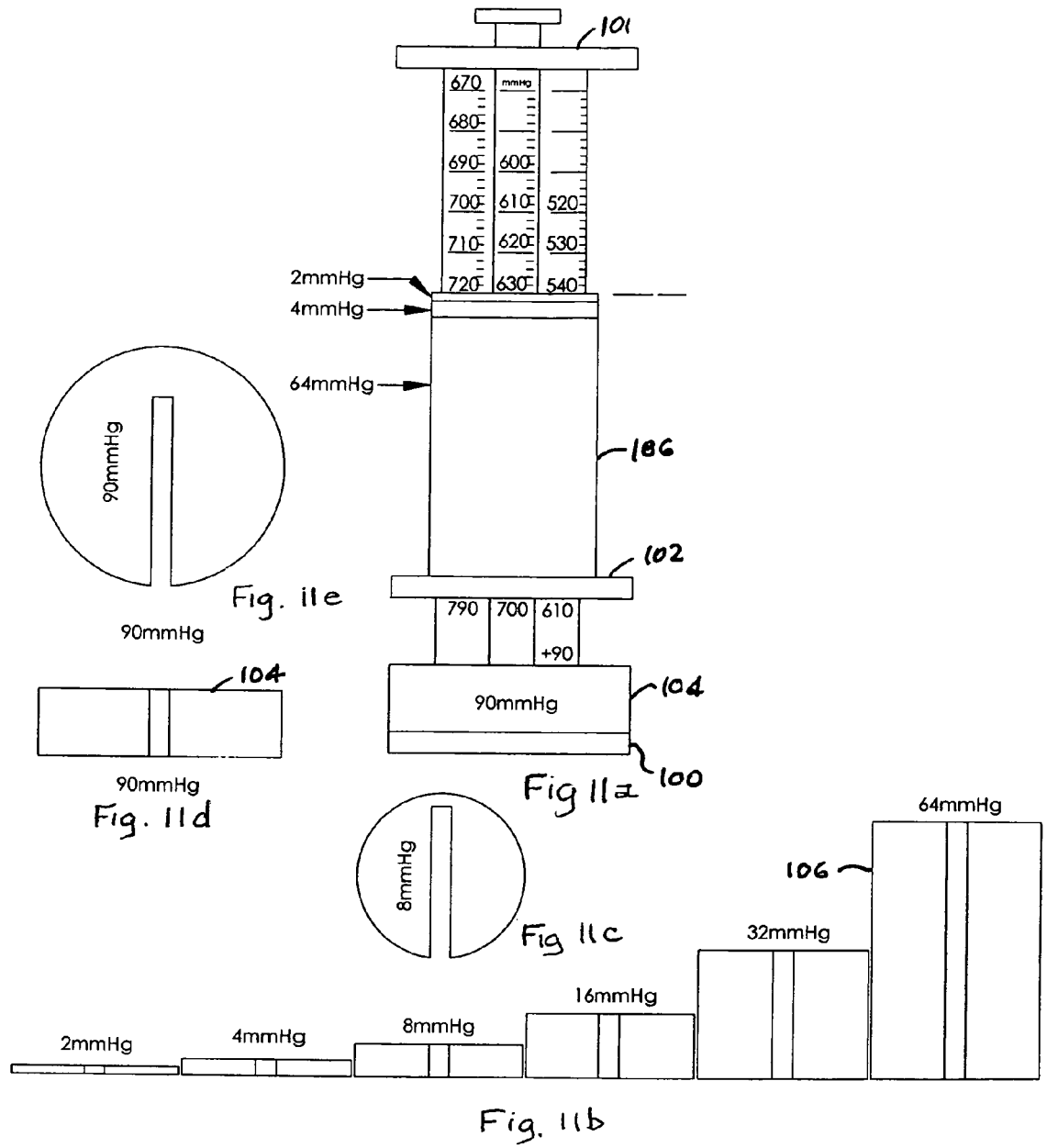
FIGS. 11a to 11e are an insert holder and a set of insert parts mounted onto the insert holder.

Referring to FIGS. 10 and 11a to 11e an embodiment of an air chamber 22 with an insert holder 101 inside the air chamber 22 is shown with a bottom shelf 100 that accepts fixed load inserts 104 (see FIG. 11a) and an upper shelf 102 that accepts a set of insert parts 106 (see FIG. 11b). There are three scales 108, 110, and 112, each being used when there are zero, one or two fixed load inserts mounted on the bottom shelf 100, respectively.

The insert holder 101 and the set of insert parts 106 are used to build a variable integrated insert as shown in FIG. 11a. The set of insert parts shown in FIG. 11b is designed to use the minimum number of insert parts to build a variable integrated insert that is equivalent to a single rod insert 24 shown in FIG. 5. FIG. 11c is a cross sectional view of each of the insert parts 106. FIG. 11e is a cross sectional view of the fixed load insert 104. To facilitate the building of the integrated insert outside the air chamber 22, the insert holder 101 has three barometric pressure scales 108, 110 and 112 that are equivalent to the three barometric pressure scales 108, 110 and 112 on the air chamber 22 in FIG. 5.

Since the preferable resolution of the barometric pressure scale for guiding the installation of an insert is 2 mm Hg, the smallest insert part is for a drop of 2 mm Hg in barometric pressure. Each insert part is marked with its corresponding barometric pressure drop for which the insert part is designed to compensate. Therefore, the smallest insert part is marked with 2 mm Hg as shown in FIG. 11b.

As shown in FIG. 10 and FIG. 5 the longest barometric pressure scale among the three scales is the scale 112, which covers a maximum barometric pressure drop of 120 mm Hg. Therefore, the complete set of the insert parts is for a drop of barometric pressure of 120 mm Hg or more. For this range of barometric pressure drop at the preferred 2 mm Hg resolution, the best set of insert parts are those that are for barometric pressure drops of 2, 4, 8, 16, 32, and 64 mm Hg, respectively. With this set of insert parts, an integrated insert can be built for any barometric pressure drop between 0-126 mm Hg at a resolution of 2 mm Hg.

Referring to FIGS. 10 and 11a-11e an example of how to build and install an integrated insert for a place where the barometric pressure is 630 mm Hg is provided. Since the barometric pressure is within the middle scale 110, the middle scale 110 is used. Therefore, one piece of the fixed load insert 104 is loaded on the bottom shelf 100. Since an integrated insert needs to be built to reach the barometric pressure level of 630 mm Hg in the middle scale 110, the insert parts 64 mm Hg, 4 mm Hg and 2 mm Hg are used. These insert parts stack up to reach the 630 mm Hg barometric pressure level just like a rod insert 24 in FIG. 5 would be pushed up to reach. After being built outside the air chamber 22, the integrated insert is inserted into and enclosed inside the air chamber 22. Then, a set button S− or S+ on the barometric pressure and measurement error monitor 50 shown in FIG. 1 is pressed multiple times till the default installation barometric pressure has been changed to 630 mm Hg.

Figure 12:
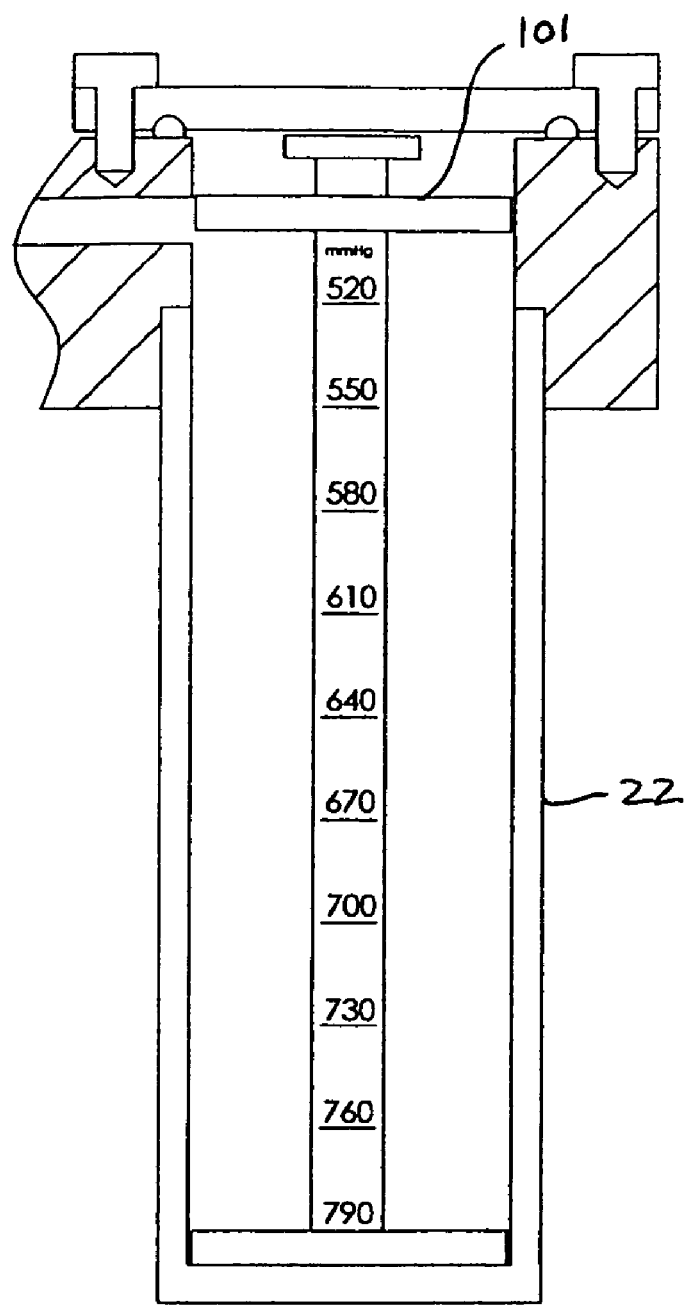
FIG. 12 is another variant of the air chamber, in which an insert holder with one barometric pressure scale on it is enclosed in the air chamber.

FIG. 12 is similar to FIG. 10 except that the scale is not broken into three sections. This allows a single set of insert parts to cover all three altitude zones shown in FIG. 10, but with lower resolution in the barometric pressure scale given the same length of air chamber 22.

Figure 13:
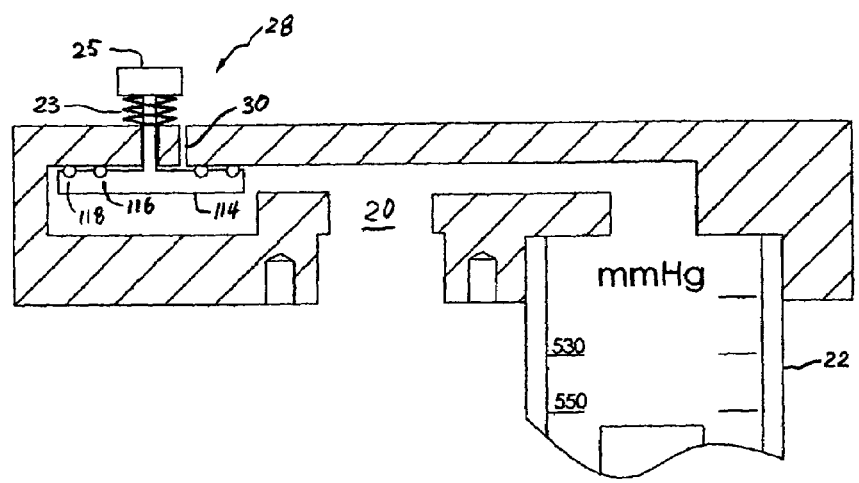
FIG. 13 is a cross-sectional view of another variant of the top manifold and manual ventilation valve, in which two o-rings are used to enhance the seal of the valve.

Referring to FIG. 13 there is shown a manual ventilation valve 28 with a disc plunger 114. The manual ventilation valve 28 is designed to take advantage of the pressure inside the air chamber 22 to better seal the air chamber 22. The disc plunger 114 is at least 12 mm in diameter, preferably about 25 mm in diameter. A larger diameter results in a larger force on the o-ring seal at a given pressure inside the air chamber 22. A larger force results in larger pressure on the o-ring, and hence a better seal. Also, two o-rings 116 and 118 are used to reduce potential leakage.

Figure 14:
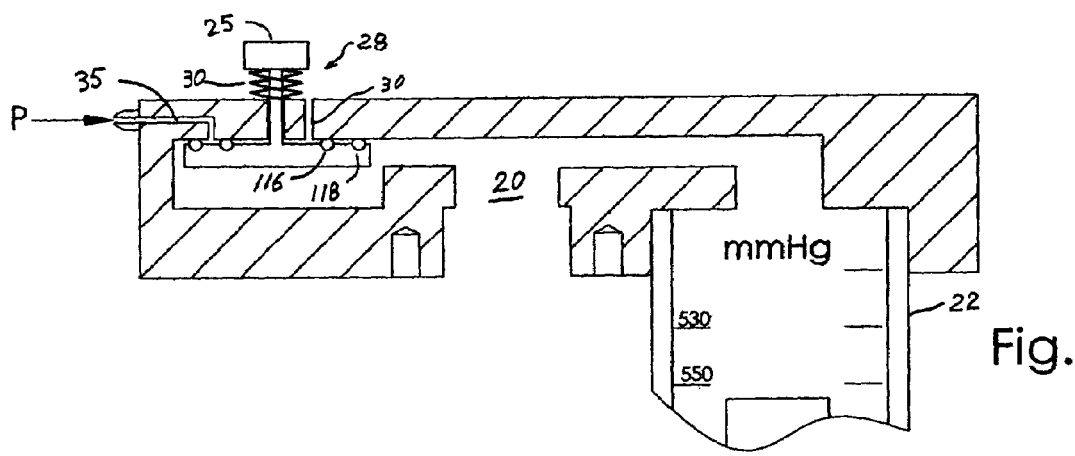
FIG. 14 is a cross-sectional view of another variant of the top manifold and manual ventilation valve, in which an equalization pressure is applied between the two o-rings to reduce the likelihood of leakage from the air chamber.

Referring to FIG. 14, an equalization pressure is introduced through a fluid channel 35 leading to a space between two o-rings 116 and 118 to enhance the seal. The equalization pressure used is the pressure to be measured. The difference between the pressure inside the air chamber 22 and the pressure to be measured is small, with the maximum difference being 300 mm $H_2O$ or about 22 mm Hg when the liquid 21 in the liquid chamber 38 is water.

Referring to FIG. 15a there is shown the elongated tube 14 having a pressure reading section 34 and a liquid offset section 36, the pressure reading section 34 having an interior surface whose diameter gradually reduces as one progresses towards the top, and the liquid offset section 36 having an offset insert 33 that is inserted into the bottom of the elongated tube 14 to forms a narrow liquid offset channel 13. At the top of the offset insert 33 there is an elastic o-ring 45 for creating a good fit between the offset insert 33 and the inside walls of the elongated tube 14. The narrow liquid offset channel 13 is created to reduce the effect of liquid offset from the zero level on pressure measurement accuracy.

FIG. 15b shows an alternative embodiment of the elongated tube 14 in which the elongated tube 14 is made with two separated pieces glued or welded together. The bottom piece includes primarily the liquid offset section 36 and may be made by an injection molding process.

Referring to FIG. 15a and FIG. 15b the elongated tube 14 has a ventilation branch 19 for coupling the fluid passageway 16 to ambient air when the liquid chamber 38 is unpressurized. In an alternative embodiment, ventilation is provided on the top of the elongated tube 16 and therefore, the branch 19 may not be needed.

Figure 16:
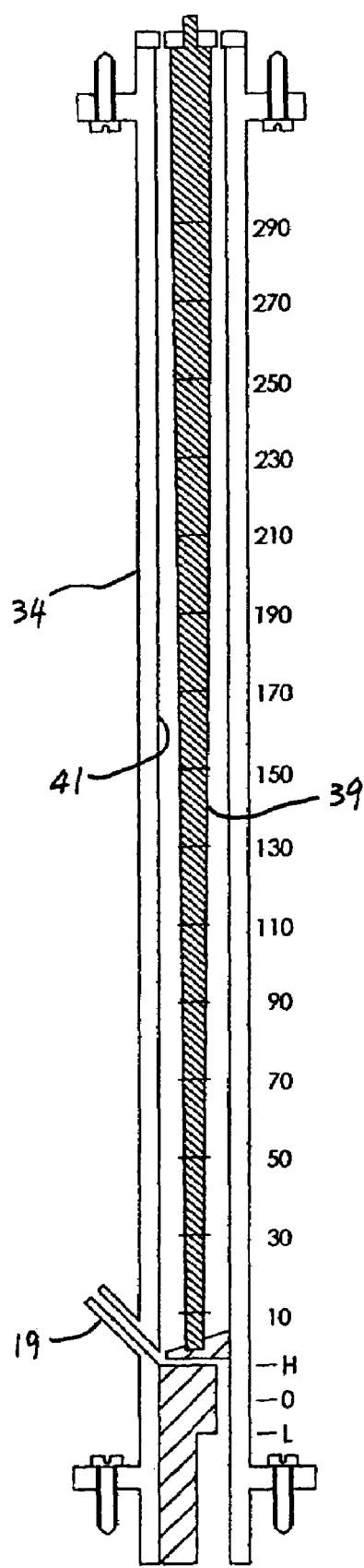
FIG. 16 is a cross-sectional view of yet another variant of the elongated tube, in which a rod with a variable diameter is inserted into a fixed-diameter tube to form a fluid passageway with variable cross sectional area.

FIG. 16 shows a reading section having a uniform diameter of its interior surface throughout its length but has a rod 39 inside whose diameter increases from the bottom to the top to create a variable cross sectional area of a fluid passageway in the reading section.

Figure 17A:
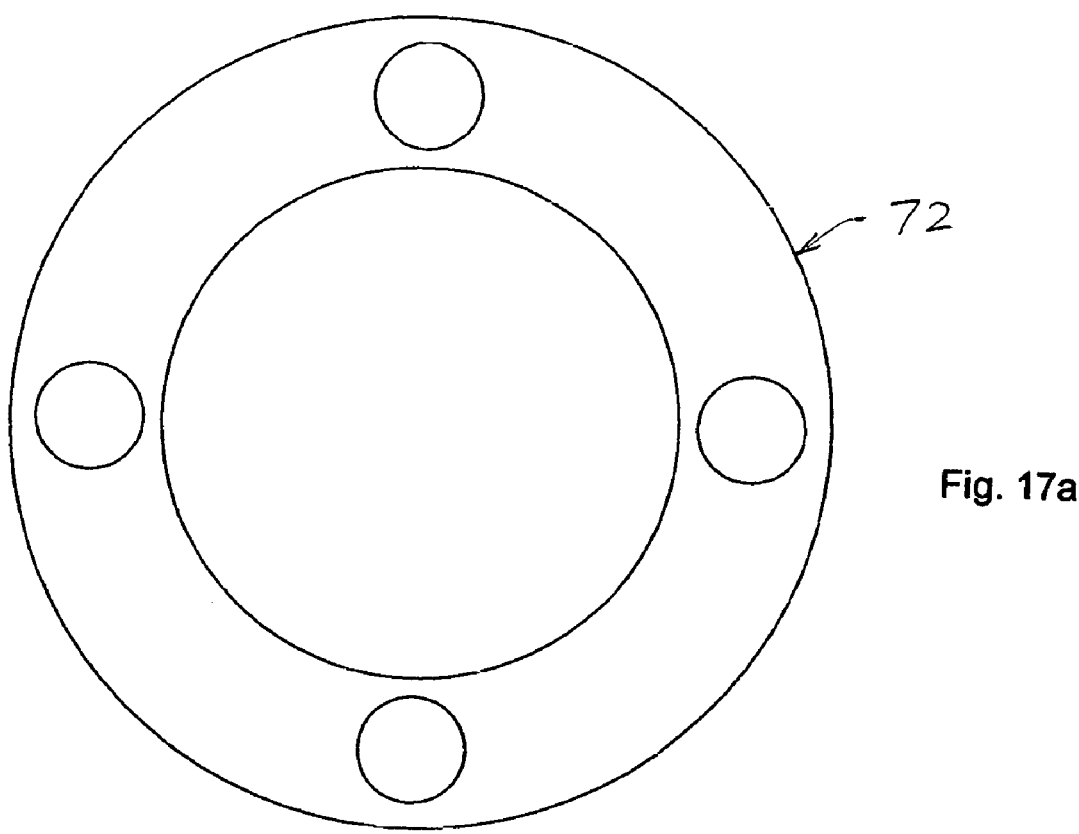
FIG. 17a is a top view of the diaphragm used in both the automatic ventilation valve and the pressure switch.
Figure 17B:
FIG. 17b is a cross-sectional view of the diaphragm in FIG. 17a shown with no pressure difference between the two sides of the diaphragm, in which the diaphragm has a symmetrically curved center part for symmetric and even movement when under pressure.

FIGS. 17a and 17b show the diaphragm 72 of the automatic ventilation valve 68. The diaphragm 54 of the pressure switch 52 is the same as the diaphragm 72 of the automatic ventilation valve 68. The diaphragm 72 of the automatic ventilation valve 68 has a symmetrically and slightly curved center part for symmetric and even distribution of force to the plunger disc 74 of the automatic ventilation valve 68 when an external pressure appears at the pressure input port 78 of the automatic ventilation valve 68.

The diaphragm 72 is made of an elastomer material including polyurethane, silicone and natural rubber, has a Shore A hardness of between 15 and 30 Durometer, and has a thickness of between 0.3 mm and 1.5 mm. Preferably, the Shore A hardness is about 25 Durometer, and the thickness is about 0.7 mm.

FIGS. 18a and 18b show the diaphragm 46 of the vapour loss reduction air valves 40 and 84, which has a cut 122 across the centre that opens in response to increased pressure on one side. The diaphragm 46 is made of an elastomer material including polyurethane, silicone and natural rubber, has a Shore A hardness of between 15 and 30 Durometer, and has a thickness of between 0.3 mm and 1.5 mm. The cut 122 has a length between 3 mm and 10 mm. Preferably, the Shore A hardness is about 25 Durometer, the thickness is about 0.7 mm, and the length of the cut is about 7 mm.

Referring to FIGS. 19a and 19b there are two holes 120 at the ends of the cut 122 of the diaphragm 46 of the vapour loss reduction air valves 40 and 84. The holes 120 prevent propagation of the cut 122 and also facilitate the opening of the cut 122 when pressure develops.

Figure 20:
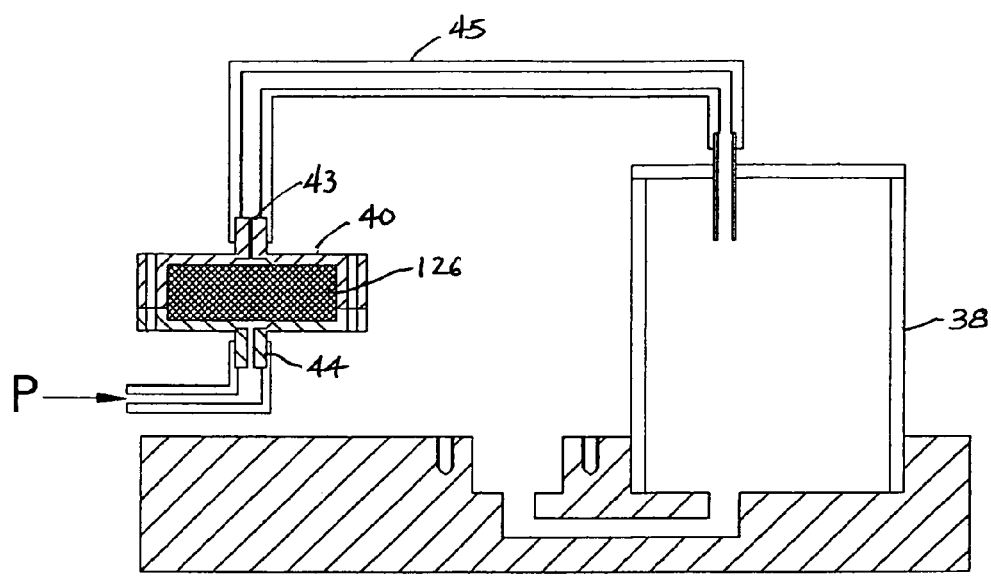
FIG. 20 is a cross-sectional view of another variant of the liquid chamber, bottom manifold and vapor loss reduction air valve, in which the vapor loss reduction air valve is formed with a small orifice and dust filter instead of a diaphragm with a cut.

Referring to FIG. 20 there is shown an alternative design in which a small orifice 43 and filter 126 replace the diaphragm 46 in the vapour loss reduction air valve 40.

Figure 21:
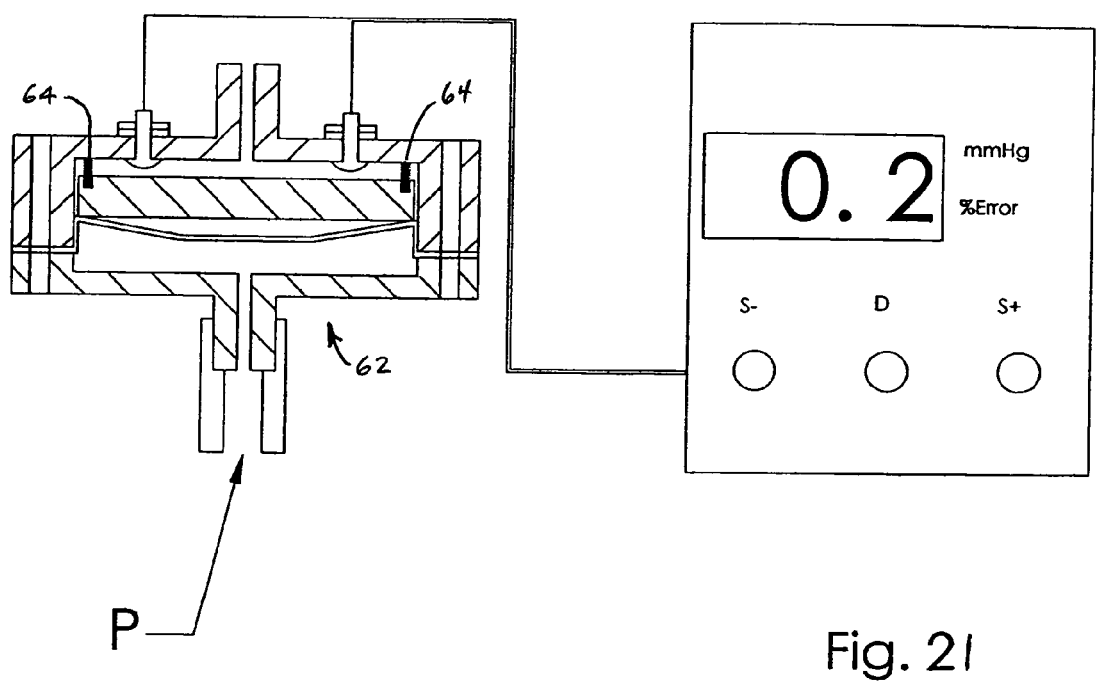
FIG. 21 is a cross-sectional view of a pressure switch and a front view of a barometric pressure and measurement error monitor, in which the pressure switch has springs added to allow it to be mounted in any orientation.

Referring to FIG. 21, a variant 62 of the pressure switch 52 adds springs 64 to mount the switch in orientations other than vertical. Without the springs 64, the switch 62 must take advantage of gravity and so can only be mounted in a vertical position.

Figure 22:
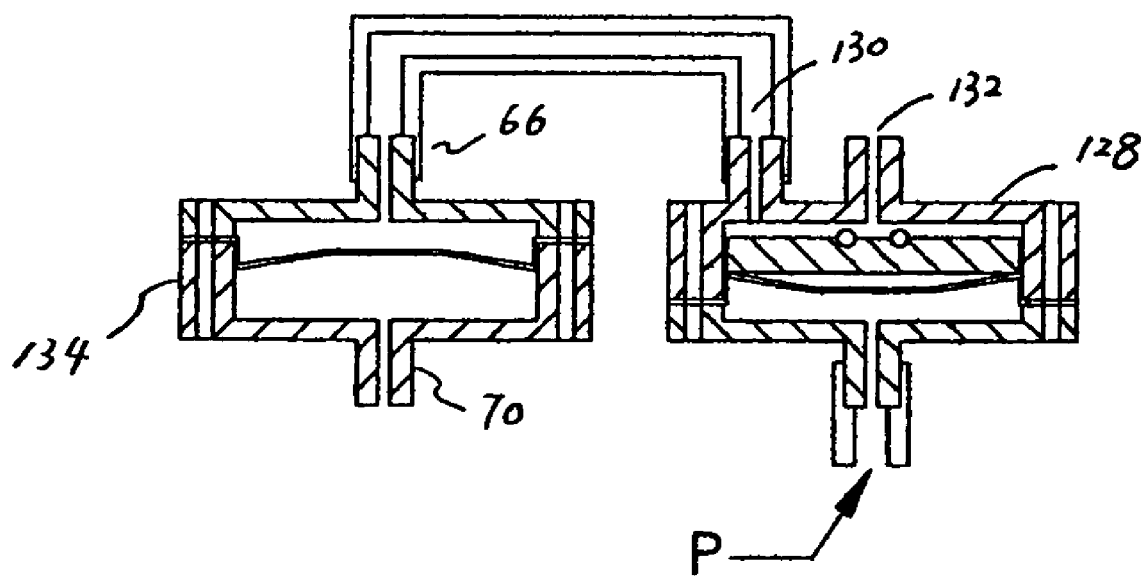
FIG. 22 is a cross-sectional view of the automatic ventilation valve and vapor loss reduction air valve in relation to each other, in which the air valve communicates directly with the ambient air pressure while the ventilation valve is in direct communication with the air inside the air chamber and fluid passageway.

FIG. 22 shows an automatic ventilation valve 128 with two ventilation ports 130 and 132. The ventilation port 132 is directly coupled through a ventilation tube 37 to the ventilation branch 19 of the elongated tube 14. A vapor loss reduction valve 134 has a port 66 that is coupled to the ventilation port 130 and an ambient air port 70 that opens to ambient air. This shows that the sequence of the valves can be changed.

Figure 23:
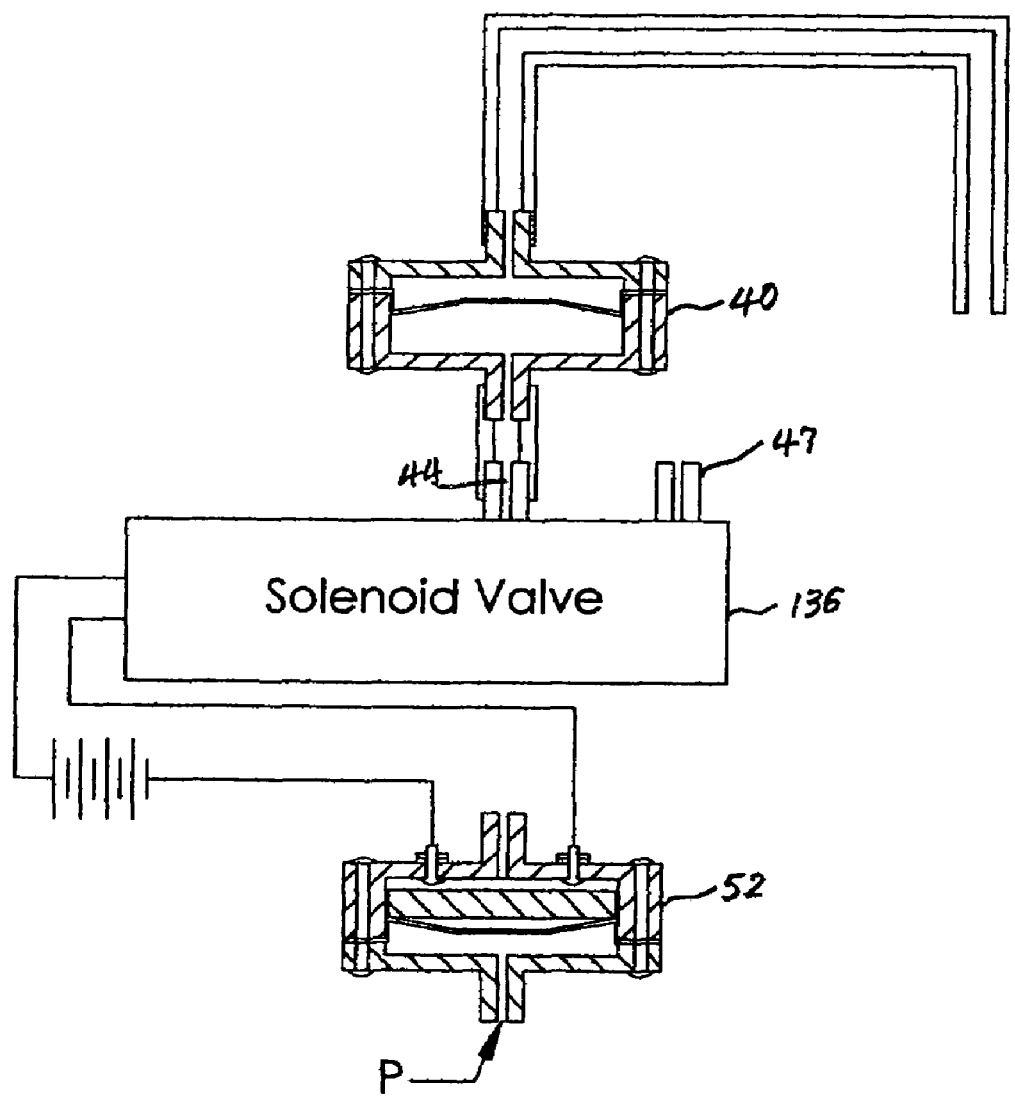
FIG. 23 is a cross-sectional view of another variant of the automatic ventilation system, in which a pressure switch and a battery powered solenoid valve are used to form an automatic ventilation system.

FIG. 23 discloses an alternative automatic ventilation valve system using a pressure switch 52 and a solenoid valve 136. An example of a solenoid valve is a two-way normally open solenoid valve of the LIF series made by the Lee Company in Westbrook, Conn., USA. When the pressure increases in the pressure input port of the pressure switch 52, the conductive disc plunger contacts the two electrical contacts and closes the circuit of the solenoid valve 136. The solenoid valve 136 turns on, and shuts off fluid communication between its two fluid ports 44 and 47.

Figure 24:
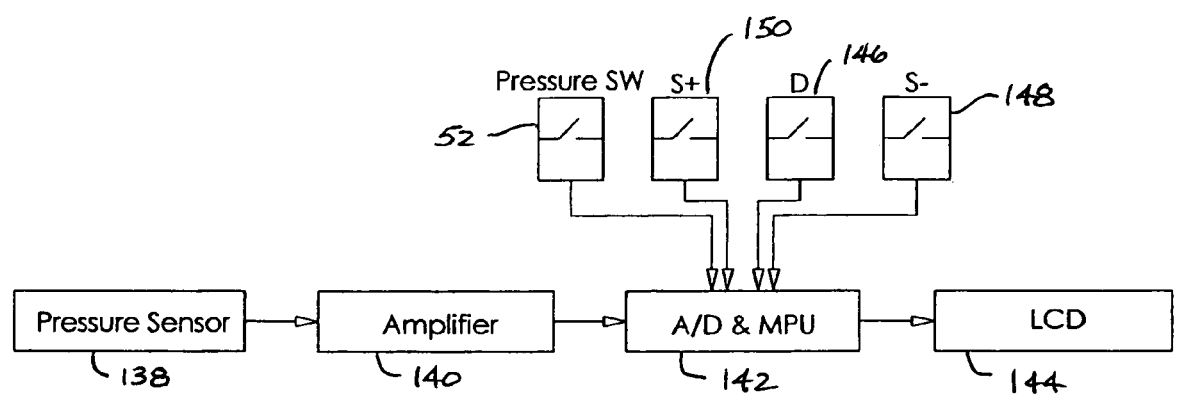
FIG. 24 is a block diagram of a barometric pressure and measurement error monitor.

FIG. 24 discloses a block diagram of a circuit for the barometric pressure and measurement error monitor 50. A pressure sensor 138 senses the barometric pressure and sends a signal to the amplifier 140, which amplifies the signal and sends the amplified signal to the micro-processor unit (MPU) 142 via a built-in A/D converter inside the MPU 142. The data is stored in the memory of the MPU.

The MPU 142 is normally in an idle mode to save power. When the pressure switch 52 is turned on, it sends a signal to the MPU 142 to wake it up and to display the error in percentage caused by the difference between the current barometric pressure and the installation barometric pressure. The result is displayed on an LCD display 144. The installation barometric pressure is the pressure set to be the default barometric pressure during the installation process. This installation barometric pressure must match the insert setting in the air chamber. For example, if the installation barometric pressure is set to 600 mm Hg, the insert 24 of the air chamber 22 must be positioned to reach the 600 mm Hg line on the scale.

The circuit also has a display button switch (D) 146, a set-to-low button switch (S−) 148 and a set-to-high button switch (S+) 150. The display button switch 146 is used to wake the MPU 142, display the current barometric pressure, the installation barometric pressure and the measurement error. The S– switch 148 is used to change the installation pressure lower and the S+ switch is used to change the installation pressure higher. The state machine 152 of the imbedded software is shown in FIG. 25.

Figure 25:
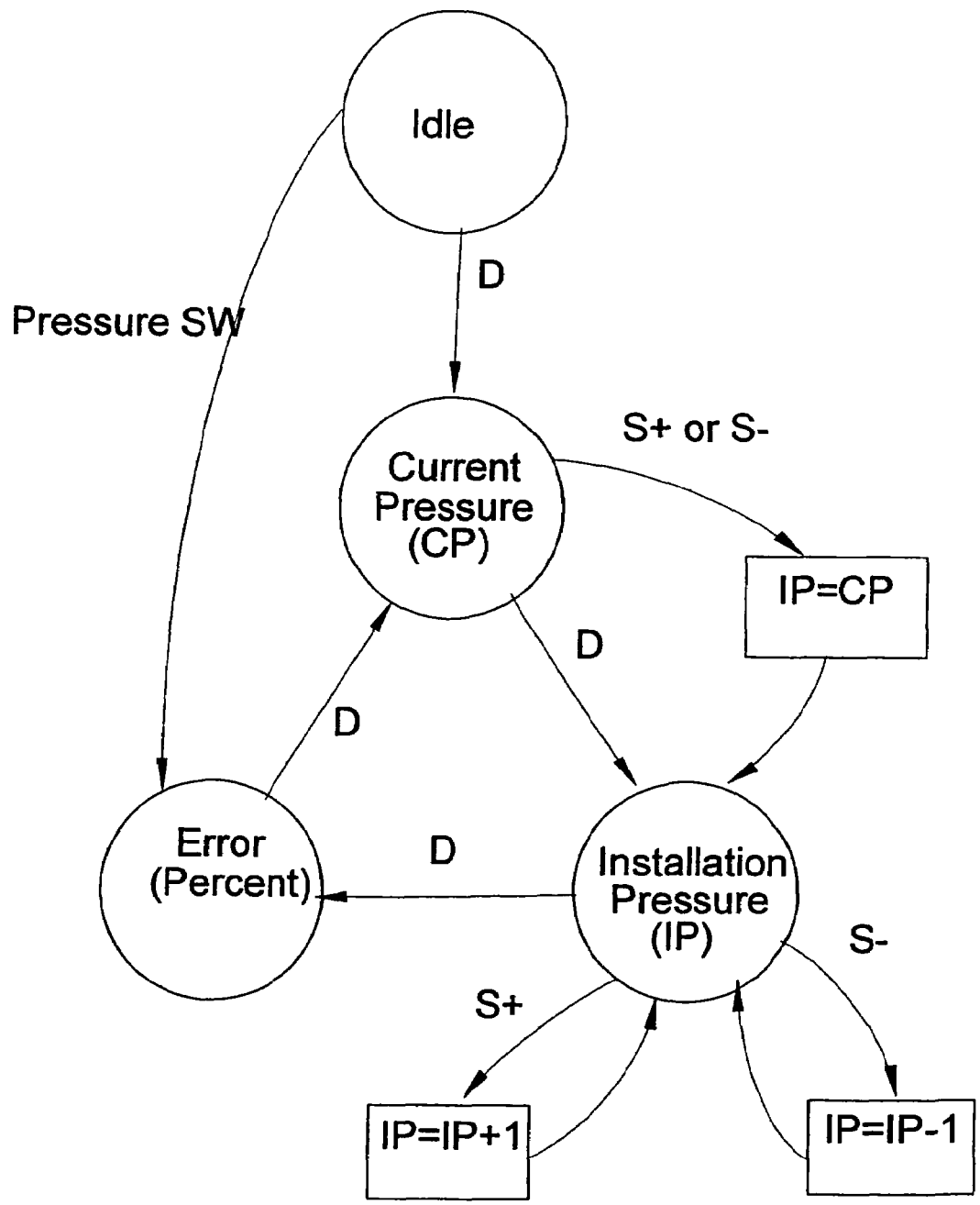
FIG. 25 is a state machine of embedded software in the barometric pressure and measurement error monitor.

FIG. 25 shows the state machine flow of operations schematically as controlled by the imbedded software in the barometric pressure and measurement error monitor 50 (see FIG. 1). The microprocessor unit (MPU) is normally in idle mode. When a Pressure Switch (Pressure SW) signal appears, the display mode changes to displaying measurement error in percentage. When the display button signal D appears, the mode changes to display the current barometric pressure (Current Pressure). At the Current Pressure mode, pressing the S– or S+ button will set the Current Pressure to the Installation Pressure and change the mode to the Installation Pressure mode. At this mode, pressing the S-button will decrease the Installation Pressure, and pressing the S+ button will increase the Installation Pressure.

Figure 26:
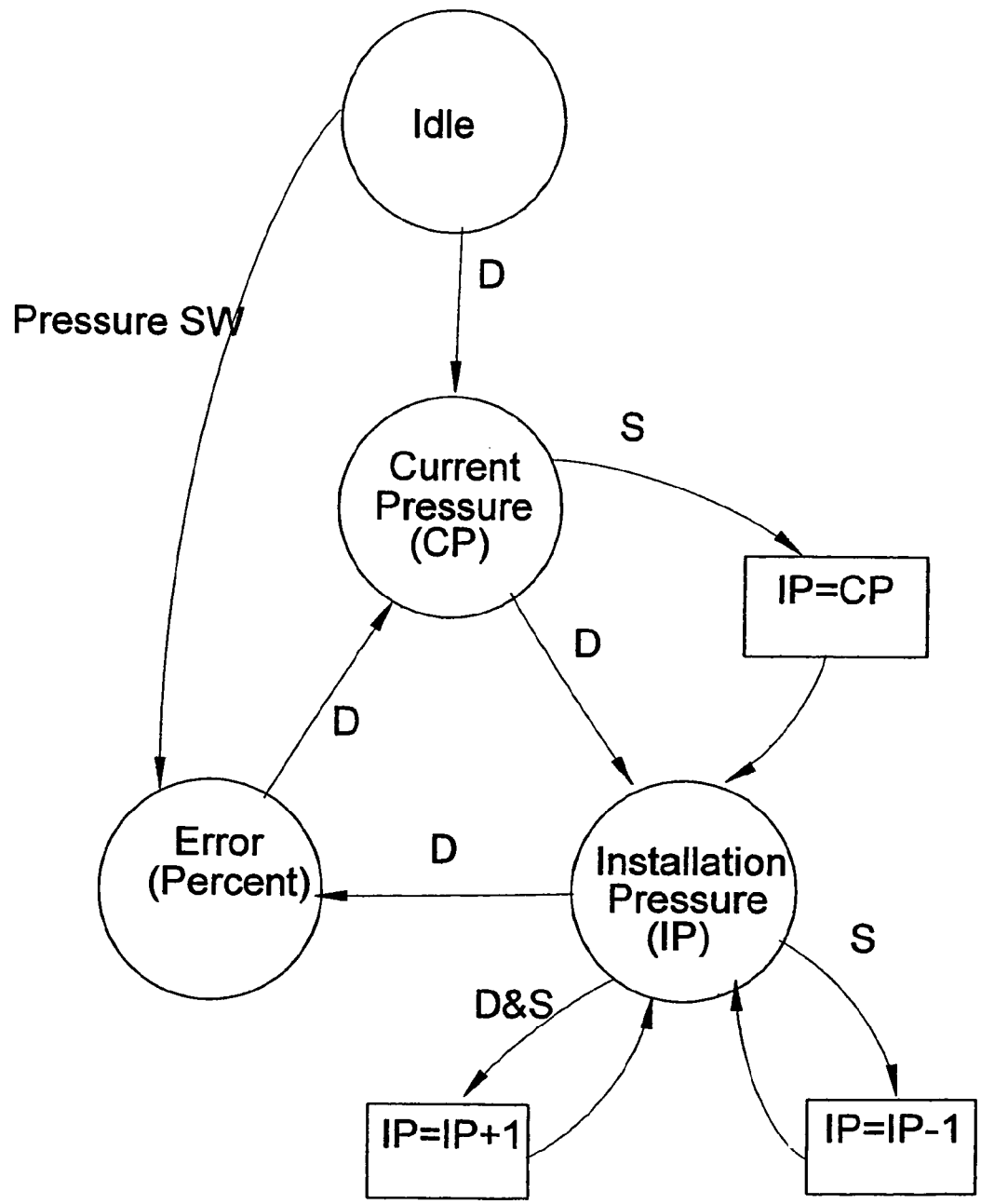
FIG. 26 is a state machine of another example of embedded software in the barometric pressure and measurement error monitor.

FIG. 26 shows an alternative implementation of the barometric pressure and measurement error monitor software. In this state machine, only one Set button (S) is used. At the Installation Pressure mode, pressing the S button will decrease the installation pressure. Pressing the D button and the S button together will increase the installation pressure.

In a preferred embodiment, a battery is used to provide power to the barometric pressure and measurement error monitor 50 so that the system can be mobile. LCD display 144 is used to save battery power. The barometer has an auto-off function that will switch the unit off in a given number of minutes ranging from 2-15 minutes after the last time the device has received any input to the device. Alternatively, a power adapter can also be used to supply power to the barometric pressure and measurement error monitor 50.

FIG. 27 is a table showing the relationship between altitude and standard barometric pressure.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

We claim:

1. A sphygmomanometer, comprising: (a) an elongated tube; (b) an air chamber coupled to a first end of said tube; (c) a liquid chamber coupled to a second end of said tube, said liquid chamber partially filled with fluid and couplable to a source of external pressure; (d) an offset section proximate the second end of said elongated tube having a liquid offset channel of a significantly reduced cross-sectional area so as to reduce the effect of fluid level changes on pressure measurement accuracy; and (e) at least one ventilation valve coupled to one of said elongated tube and said air chamber operative to vent said elongated tube and said air chamber to atmosphere, including a pressure switch coupled to an external pressure source and a barometric pressure and pressure error monitor coupled to said pressure switch and wherein said pressure switch on closing, closes an electrical circuit coupled to said barometric pressure and pressure error monitor causing said barometric pressure and pressure error monitor to become activated.

2. A sphygmomanometer according to claim 1, including a vapour loss reduction air valve intermediate said liquid chamber and an external pressure source, operative to reduce vapour loss and to permit the passage of air between said external pressure source and said liquid chamber.

3. A sphygmomanometer according to claim 1, wherein a cross section of an interior surface of said elongated tube varies along its length to compensate for non-linearity in Boyle's law so as to linearly display pressure.

4. A sphygmomanometer according to claim 1, including a pressure switch coupled to said liquid chamber and operative to switch on said barometric pressure and pressure error monitor upon being pressurized.

5. A sphygmomanometer according to claim 4, wherein said barometric pressure and pressure error monitor displays, upon being switched on, a difference between current barometric pressure and an installation barometric pressure as a percentage of an installation barometric pressure.

6. A sphygmomanometer according to claim 4, wherein said pressure switch includes a diaphragm responsive to pressure from said liquid chamber, and a plunger plate with a first side for receiving a force from said diaphragm under pressure and a second side for electrically shorting two electrical contacts upon moving in response to said force.

7. A sphygmomanometer, comprising: (a) an elongated tube; (b) an air chamber coupled to a first end of said tube; (c) a liquid chamber coupled to a second end of said tube, a portion of which is filled with non-toxic liquid; (d) one of a sliding insert, screw insert and integrated insert insertable into said air chamber and one of a barometric pressure and altitude scale on said air chamber or said one insert according to which said one insert adjusts a volume of air in said air chamber; and (e) a ventilation valve coupled to one of said elongated tube and said air chamber operative to vent said elongated tube and said air chamber to ambient air pressure upon being open and to seal said elongated tube and said air chamber against ambient air upon being closed, including pressure switch coupled to an external pressure source and a barometric pressure and pressure error monitor coupled to said pressure switch, wherein said pressure switch on closing, closes an electrical circuit coupled to said barometric pressure and pressure error monitor causing said barometric pressure and pressure error monitor to become activated.

8. A sphygmomanometer according to claim 7, including a vapour loss reduction air valve intermediate said liquid chamber and an external pressure source, operative to block vapour loss and to permit the passage of air between said external pressure source and said liquid chamber.

9. A sphygmomanometer according to claim 7, wherein a cross section of an interior surface of said elongated tube varies along its length to compensate for non-linearity in Boyle's law so as to linearly display pressure.

10. A sphygmomanometer according to claim 7, wherein said barometric pressure and pressure error monitor displays, upon being switched on, a difference between a current barometric pressure and an installation barometric pressure as a percentage of an installation barometric pressure.

11. A sphygmomanometer according to claim 10, wherein said pressure switch includes a diaphragm responsive to pressure from said liquid chamber, and a plunger plate with a first side for receiving a force from said diaphragm under pressure and a second side for electrically shorting two electrical contacts upon moving in response to said force.

12. A sphygmomanometer according to claim 10, including a barometric pressure and pressure error monitor and wherein said pressure switch on closing, closes an electrical circuit coupled to said barometric pressure and pressure error monitor.

13. A sphygmomanometer, comprising: (a) an elongated tube; (b) an air chamber coupled to a first end of said elongated tube; (c) a liquid chamber coupled to a second end of said elongated tube, a portion of which is filled with liquid; (d) an automatic ventilation valve coupled to said elongated tube, normally open to atmosphere and responsive to an increase in pressure of an external pressure source to close and, in response to a drop in pressure back to atmospheric pressure of said air chamber, to re-open, wherein said liquid is non-toxic, including a pressure switch and a barometric pressure and pressure error monitor coupled to said pressure switch wherein said pressure switch closes in response to an increasing source pressure and closes an electrical circuit coupled to said barometric pressure and pressure error monitor causing the latter to become activated.

14. A sphygmomanometer according to claim 13, wherein said barometric pressure and pressure error monitor displays, upon being switched on, a difference between a current barometric pressure and an installation barometric pressure as a percentage of an installation barometric pressure.

15. A sphygmomanometer, comprising: (a) an elongated tube having a fluid passageway of varying cross sectional area along the length of the fluid passageway; (b) an air chamber coupled to a first end of said tube; (c) a liquid chamber coupled to a second end of said tube and couplable to a source of external pressure; (d) an insert insertable into said air chamber for adjusting a volume of air in said air chamber; and (e) a ventilation valve counted to one of said elongated tube and said air chamber operative to vent said elongated tube and said air chamber to atmosphere, including pressure switch coupled to an external pressure source and a barometric pressure and pressure error monitor coupled to said pressure switch, wherein said pressure switch on closing, closes an electrical circuit coupled to said barometric pressure and pressure error monitor causing said barometric pressure and pressure error monitor to become activated.

16. A sphygmomanometer, comprising: (a) an elongated tube having a fluid passageway of varying cross sectional area along the length of the fluid passageway; (b) an air chamber coupled to a first end of said tube; (c) a liquid chamber coupled to a second end of said tube and couplable to a source of external pressure; (d) an insert insertable into said air chamber for adjusting a volume of air in said air chamber; and (e) a ventilation valve coupled to one of said elongated tube and said air chamber operative to vent said elongated tube and said air chamber to atmosphere, including a vapour loss reduction air valve intermediate said liquid chamber and an external pressure source, operative to block vapour loss and to permit the passage of air between said external pressure source and said liquid chamber.

\* \* \* \* \*